United States Patent [19]

Arnold, Jr. et al.

[11] Patent Number: 5,599,667

[45] Date of Patent: Feb. 4, 1997

[54] POLYCATIONIC SUPPORTS AND NUCLEIC ACID PURIFICATION SEPARATION AND HYBRIDIZATION

[75] Inventors: Lyle J. Arnold, Jr.; Norman C. Nelson, both of San Diego; Mark A. Reynolds, La Jolla; Alexander A. Waldrop, III, San Diego, all of Calif.

[73] Assignee: Gen-Probe Incorporated, Sna Diego, Calif.

[21] Appl. No.: 311,289

[22] Filed: Sep. 23, 1994

Related U.S. Application Data

[63] Continuation of Ser. No. 893,895, Jun. 4, 1992, abandoned, which is a continuation of Ser. No. 294,689, filed as PCT/US88/00550, Mar. 2, 1988, abandoned, which is a continuation-in-part of Ser. No. 20,866, Mar. 2, 1987, abandoned.

[51] Int. Cl.⁶ .......................... C12Q 1/68; C12N 15/10
[52] U.S. Cl. ..................... 435/6; 536/23.1; 536/24.3
[58] Field of Search .................. 435/6; 536/24.3, 536/23.1

[56] References Cited

U.S. PATENT DOCUMENTS

| | | | |
|---|---|---|---|
| 4,219,411 | 8/1980 | Yen et al. | 209/213 |
| 4,469,863 | 9/1984 | Tsó et al. | 536/24.5 |
| 4,486,539 | 12/1984 | Ranki | 436/504 |
| 4,554,088 | 11/1985 | Whitehead et al. | 252/62.54 |
| 4,563,419 | 1/1986 | Ranki | 435/6 |
| 4,652,517 | 3/1987 | Scholl et al. | 435/5 |
| 4,672,040 | 6/1987 | Josephson | 436/526 |
| 4,698,302 | 10/1987 | Whitehead et al. | 435/94 |
| 4,745,077 | 5/1988 | Holian et al. | 436/526 |

FOREIGN PATENT DOCUMENTS

| | | |
|---|---|---|
| 0130523 | 6/1984 | European Pat. Off. . |
| 0139489 | 9/1984 | European Pat. Off. . |
| 8400508 | 7/1982 | WIPO . |
| WO865519 | 3/1986 | WIPO . |

OTHER PUBLICATIONS

Kanter et al. Analytical Biochemistry 97 77–84 (1979).
Bio Rad Price List 1984 pp. 42–44, see especially p. 43.
Pharmacia Ion Exchange Chromatography: principles and methods (1983); Rahmsi Lund, Sweden pp. 4 and 54.
Focus: BRL 6:2 pp. 7, 8, 10 Apr. 1984.
Focus: BRL 6:3 pp. 7 & 8 Jul. 1984.
Focus: BRL 6:4 p. 8 Oct. 1984.
Focus: BRL 4:2 p. 9 Sep. 1982.
Focus: BRL 4:3 p. 13 Dec. 1982.
Focus: BRL 5:2 p. 10 Jun. 1983.
Focus: BRL 5:3 p. 10 Sep. 1983.
Sambrook et al, Molecular Cloning: A Laboratory Manual, Second Edition, Cold Spring Harbor Laboratory Press, 1989, p. E.30.
Wells et al Methods in Enzymology 65:627–47 (1980).
Kelmers et al Methods in Enzymology 20:9–34 (1971).
Parish; Principles & Practice of Experiments with Nucleic Acids (1972) Longman Group Limited; London, Great Brittain pp. 160–171, 360–371.
Scopes; Protein Purification (1982); Springer–Verlag, N.Y. NY pp. 138–139.
Thompson et al.; Methods in Enzymology 100 (1983) Academic Press Inc NY NY pp. 368–399.
Focus: BRL 4:1 p. 13 Jun. 1982.
Chemical Abstracts, vol. 107, No. 23, issued Dec. 7, 1987 by J. Summerton, Abstract No. 214481.
Scott & Kuhns, Analytical Biochem., 47:471–478 (1972).
Nygaard, A. P. & Hall, B. D. J. Mol. Biol., 9:125–142 (1964).
Shih & Martin, Biochemistry, 13:3411–3418 (1974).
Enea & Zinder, Science, 190:584–586 (1975).
Shih & Khoury, Biochemistry, 15:487–493 (1976).
Longacre S. & Mach B., J. Biol. Chem., 253:7500–7507 (1978).
Goldberg, et al., Methods in Enzymol., 68:206–242 (1979).
Kreig, et al., Analytical Biochem., 134:288–294 (1983).
Gatreau, et al., Analytical Biochem., 134:320–324 (1983).
Pearson, et al., Biochem. Biophys. Acta., 228:770–774 (1971).
Shum & Crothers, Nucl. Acids Res., 5:2297–2311 (1978).
Narihara, et al., J. Chromatog., 236:513–518 (1982).
Colpan & Riesner, J. Chromatog., 296:339–353 (1984).
Hecker, et al., J. Chromatog., 326:251–261 (1985).
Muller, Eur. J. Biochem., 155:203–212 (1986).
Johnson, et al., Biotechniques, 4:64–70 (1986).
Guenther, et al., Fed. Proc., 44:1622 (abs 7086) (1985).
Ruth, et al., Fed. Proc., 44:1622 (abs. 7088) (1985).
Nygaard & Hall, Biochem. Biophys. Res. Commun., 12:98–104 (1963).
Gillespie & Spiegelman, J. Mol. Biol., 12:829–842 (1965).
Denhardt, Biochem. Biophys. Res. Commun., 23:641–646 (1966).
Britten & Kohne, Carnegie Inst. Washington Yearbook, 65, 78 (1966).
Brenner, et al., Anal. Biochem., 28, 447–459 (1969).
Hunger, et al., Biochem. Biophys. Acta., 653: 344–349 (1981).
Seed, Nucl. Acids Res., 10: 1799–1811 (1982).
Leary, et al., P.N.A.S. USA, 80: 4045–4049 (1983).
Dunn & Sambrook, Methods in Enzymol., 65:468–478 (1980).
Palva A. M., Jour. Clin. Micro., 18:92–100 (1983).
Virtanen, et al., Lancet, 381–383 (1983).
Ranki, et al., Gene, 21:77–85 (1983).
Polsky–Cynkin, et al., Clin. Chem., 31:1438–1443 (1985).
Preface and Chapter 1 from the book "Nucleotide Analogs", 1980.
Kornberg, "DNA Replication", p. 53, 1974.
Ninth New Collegiate Dictionary, definition of "analogue".
Webster's II New Riverside University Dictionary, definition of "analogue".

*Primary Examiner*—John L. LeGuyader
*Attorney, Agent, or Firm*—Lyon & Lyon

[57] ABSTRACT

Described herein is the use of polycationic solid supports in the purification of nucleic acids from solutions containing contaminants. The nucleic acids non-covalently bind to the support without significant binding of contaminants permitting their separation from the contaminants. The bound nucleic acids can be recovered from the support. Also described is the use of the supports as a means to separate polynucleotides and hybrids thereof with a nucleotide probe from unhybridized probe. Assays for target nucleotide sequences are described which employ this separation procedure.

73 Claims, No Drawings

POLYCATIONIC SUPPORTS AND NUCLEIC ACID PURIFICATION SEPARATION AND HYBRIDIZATION

This application is a continuation of application Ser. No. 07/893,895, filed Jun. 4, 1992, abandoned, which is a continuation of application Ser. No. 07/294,689, filed Nov. 2, 1988 which is the national filing of PCT/US88/005500, filed Mar. 2, 1988, which is a continuation-in-part of U.S. Ser. No. 07/020,866, filed Mar. 2, 1987, now abandoned.

1. FIELD OF THE INVENTION

This invention relates to polycationic supports and their use for purifying nucleic acids, immobilizing nucleic acids for hybridization procedures, and selectively separating relatively large hybridized polynucleotides from solution without significantly removing unhybridized smaller polynucleotide or oligonucleotide probes.

2. DESCRIPTION OF THE PRIOR ART

In recent years, the desire to purify polynucleotides and to conveniently carry-out hybridization reactions to detect specific nucleotide sequences in polynucleotides has increased dramatically. For this reason, numerous methods have been developed for separating polynucleotides and their hybrids and for detecting specific target nucleotide sequences in polynucleotides employing polynucleotide or oligonucleotide probes.

In the area of polynucleotide purification, procedures are employed to either purify polynucleotides prior to hybridization or to remove biological contaminants which might interfere with various biochemical procedures. Historically, different methods have been employed such as phenol extraction, ethanol precipitation, gel electrophoresis, gel permeation Shih & Martin, *Biochemistry*, 13:3411–3418 [1974]; Enea & Zinder, *Science*, 190:584–586 [1975]; Shih & Khoury, *Biochemistry* 15:487–493, [1976]; Longacre & Mach, *J. Biol. Chem.* 253:7500–7507 [1978]; Goldberg et el., *Methods in Enzymol.*, 68:206–242 [1979]; Kreig et al., *Analytical Biochem.*, 134:288–294 [1983]; and Gautreau, et el., *Analytical Biochem.*, 134:320–324 [1983]).

More recently, high pressure liquid chromatography has been used for preparative scale purifications of single and double stranded polynucleotides. Anion exchange columns employed in this method include RPC-5 (Pearson et el., *Biochem. Biophys. Acta.*, 228, 770–774,[1971]), other coated supports incorporating Kel-F (Shum and Crothers, *Nucl. Acids Res.*, 5, 2297–2311, [1978]) or siliconized glass beads (Narihara et el., *J. Chromatog.*, 236, 513–518, [1982]) and diethylamino-ethyl-derivatized silica such as Nucleogen[1]/ (Colpan and Riesner, *J. Chromatog.*, 296, 339–353, [1984]; Hecker et el., *J. Chromatog.*, 326, 251–261, [1985]; and Muller, *Eur. J. Biochem.*, 155, 203–212, [1986]).

[1]/ Nucleogen is a registered trademark of Macherey-Nagel, Duren, West Germany.

In addition, other recent methods of purification include both the selective adsorption of polynucleotides to surfaces of specialized supports (Johnson et al., *Biotechniques*, 4, 64–70 [1986], Guenther et al., *Fed. Proc.*, 44, 1622 (abs. 7086) [1985] and immobilization of polynucleotides by complementary nucleic acid sequences (Nanibhushan & Crothers, Eur. Pat. App. No. 130, 523 [1985]; Ruth et el., *Fed. Proc.* 44, 1622 (abs. 7088), 1985; Blakesley and Thompson, Int. Pat. App. No. PCT/US84/00508 [1985]).

The purification methods mentioned above, however, continue to suffer from one or more of the following limitations, particularly when adapting them to a clinical environment. These limitations include: They are time consuming or laborious; they do not quantitatively recover the desired polynucleotides; they are not compatible with clinical samples; or they cannot be easily interfaced to automated systems.

In addition to purifying polynucleotides, solid supports have been used for separating hybrids of a polynucleotide and a nucleotide probe from unhybridized polynucleotide or oligonucleotide probes. Hybridization of polynucleotides in conjunction with appropriately labeled polymeric nucleotide probes has long been recognized as a specific and sensitive method for detecting unique or misexpressed polynucleotide target sequences. This ability permits the detection of infectious organisms such as bacteria, viruses, parasites and fungi; genetic diseases such as sickle cell anemia; and various cancers. However, the inability to rapidly and conveniently separate hybridized from unhybridized polynucleotides has limited the use of hybridization procedures in clinical diagnosis and the research environment.

For more than twenty years, researchers have been working to develop methods to identify the presence of "target" polynucleotides employing hybridization. These methods have largely been based upon separating polynucleotide hybrids from unhybridized polynucleotide or oligonucleotide probe molecules. In 1963 and 1964, Nygaard & Hall (*Biochem. Biophys Res. Commun.*, 12, 98 [1963]; *J. Mol. Biol.*, 9, 125 [1964] reported a method for separating DNA/RNA hybrids by filtration through nitrocellulose. These researchers found that single and double stranded RNA did not stick to nitrocellulose, but that single stranded DNA or DNA complexed to RNA did stick to nitrocellulose. Thus, a reaction between radiolabeled RNA and unlabeled DNA could be monitored by measuring the amount of radioactivity caught on the filter.

This procedure was followed by one described by Gillespie and Spiegelman, (*J. Mol. Biol.*, 12, 829 [1965]) wherein single stranded DNA was immobilized on nitrocellulose filters and hybridized with a solution containing radiolabeled RNA. After removal of excess RNA, the degree of hybridization was determined by the amount of radiolabel immobilized on the filter.

The following year, Denhardt (*Biochem. Biophys. Res. Commun.*, 23, 641 [1966] reported the development of a similar system whereby single-stranded DNA was immobilized to nitrocellulose, the filter "capped" to reduce nonspecific background, and the immobilized DNA hybridized with a solution containing an appropriate radiolabeled DNA probe. This has remained as one of the more preferred hybridization procedures to date. This procedure, however, is laborious and time consuming; normally requiring more than a day to complete.

In addition to nitrocellulose, hydroxyapatite has been used to separate single stranded and double stranded polynucleotide species. Britten and Kohne, for example, (*Carnegie Inst. Washington Yearbook*, 65, 78 [1966]) used hydroxyapatite to separate [$^{32}$P]-labeled *E. coli* DNA fragments which were hybridized from *E. coli* DNA fragments which were not hybridized. These methods were further refined by Brenner et al. (*Anal. Biochem.*, 28, 447 [1969]), to carry out separations in test tubes.

Other procedures have been developed in an effort to further improve immobilization of DNA and RNA for hybridization reactions. These include fixation of DNA and RNA to cyanuric chloride-activated paper (Hanger et al., *Biochem. Biophys. Acta*, 653, 344 [1981]) and aryldiazonium cellulose papers (Seed, *Nucl. Acids Res.,* 10, 1799 [1982]).

Procedures have also been described for visualizing non-isotopically labeled biotinylated probes hybridized to DNA or RNA immobilized on nitrocellulose (Leary et al., *Proc. Natl. Acad. Sci. U.S.A.,* 80, 4045 [1983]). This procedure, however, is even more laborious than previous protocols employing radiolabels since it requires additional "capping" and washing steps.

In an effort to improve the detection of "target" polynucleotide employing hybridization, numerous procedures have been developed employing a double (sandwich) hybridization. Usually an immobilized polynucleotide is employed to find the target polynucleotide followed by hybridization with a second polynucleotide which is labelled (Dunn & Sambrook, *Methods. Enzymol.,* 65, 468–478 [1980]; Palva, *Journal Clin. Micro.,* 18, 92–100 [1983]; Virtanen et al., *Lancet,* 381–383 [1983]; Ranki et al., *Gene,* 21, 77–85 [1983]; Ranki & Soderland, U.S. Pat. No. 4,486, 539 [1984]; Polsky-Cynkin et al., *Clin. Chem.,* 31, 1438–1443 [1985]; Ranki & Soderlund U.S. Pat. No. 4,563, 419 [1986]).

In one application of the sandwich assay procedure, both hybridization reactions are carried out in solution followed by separation on immobilized streptavidin which separates the entire polynucleotide sandwich using a biotin labeled probe (Hansen & Jones, E.P.O. 0 139 489 [1985]).

The hybridization systems described above still lack the ease of handling and speed to make hybridization assay procedures widely useful in a clinical environment. They are generally time consuming, laborious and are lacking in sensitivity. In addition, many of them are incompatible with agents contained in biological samples and they cannot be readily automated.

3. DEFINITIONS

As used in this disclosure, the following terms are defined as:

nucleotide: a subunit of a nucleic acid consisting of a phosphate group, a 5 carbon sugar and a nitrogen containing base. In RNA the 5 carbon sugar is ribose. In DNA, it is 2-deoxyribose.

nucleotide multimer: a chain of nucleotides linked by phosphodiester bonds.

oligonucleotide: a nucleotide multimer generally about 10 to about 100 nucleotides, but which may be 200 or more nucleotides in length. They are usually synthesized from nucleotide monomers or obtained by enzymatic means.

polynucleotide: a nucleotide multimer generally about 100 nucleotides or more in length.

nucleotide probe: a nucleotide multimer having a nucleotide sequence complementary with a target nucleic acid sequence contained within a second nucleotide multimer, usually a polynucleotide, having diagnostic significance. Usually the probe is selected to be perfectly complementary to the target sequence. However, in some cases it may be adequate or even desirable that one or more nucleotides in the probe not be complementary to the corresponding base in the target sequence. A nucleotide probe is also usually a smaller multimer than the multimer containing the target sequence. Typically it is an oligonucleotide, but may be a polynucleotide and is usually labeled with a chemical substituent which permits its detection, for example, by radiometric colorimetric, fluorometric, chemiluminescence or other suitable techniques.

separation solution: A solution having a composition which permits immobilization of a nucleotide multimer, usually a polynucleotide, or a hybrid thereof to a cationic solid support as described herein without binding contaminants including in certain cases, smaller polynucleotides and oligonucleotides. When a polynucleotide hybridized with a probe is being immobilized, the separation solution has the additional property of inhibiting binding of the nucleotide probe to the support.

wash solution: A solution with a composition to permit removal of excess nucleotide probe or contaminants without significantly removing a desired nucleotide multimer, usually a polynucleotide or a desired polynucleotide hybrid, from the surface of a cationic solid support as described herein. The composition of a wash solution may, in some cases, be the same as a separation solution.

elution solution: A solution designed to liberate a nucleotide multimer such as a polynucleotide, a hybridized polynucleotide, or a labeled nucleotide probe, or a specific label from the surface of a cationic solid support, the specific liberation done being dependent upon the desired kind of recovery from the solid support that is desired.

hybridization solution: A solution designed to permit a desired hybridization to occur. The desired hybridization is typically between a polynucleotide and a probe for a target sequence. Therefore, when hybridization occurs with a polynucleotide previously immobilized on a cationic solid support, this solution has the additional property of minimizing the non-specific binding of the nucleotide probe to the support.

4. SUMMARY OF THE INVENTION

This invention is based upon the discovery that polycationic solid supports can be used to selectively adsorb nucleotide multimers according to their size, larger multimers being more tightly bound to the support than smaller ones. The binding interaction is believed to be based, at least in part, on the ionic attractive forces between a positively charged support and the negatively charged sugar phosphate backbone of the nucleotide multimer. These properties may be employed in batch procedures to both rapidly purify polynucleotide and separate hybrids thereof from complex solutions.

One method according to the invention permits purification of nucleotide multimers in solutions containing various constituents of the organism from which the multimers are obtained including multimers of lower molecular weight, by adsorbing the desired multimers to the polycationic support. In the case of clinical samples, the nucleotide multimers are also removed from other constituents of the body fluids and tissues from which the multimers are to be separated. After separation of the solid support from the solution, the multimers may be eluted from the support.

In another method according to the invention useful in hybridization procedures to detect relatively long polynucleotides with shorter, labeled nucleotide probes, the polycationic support can be used to separate polynucleotides, and hybrids thereof with the probe, from the unhybridized probe. In a presently preferred embodiment of this method, the probe is added to a solution containing polynucleotides and hybridization allowed to occur prior to immobilization. After hybridization with the probe, the solution is contacted with the support to adsorb the polynucleotides, including any hybrid thereof with the probe. In a presently less preferred embodiment, the polycationic support is added to the solution containing polynucleotides to adsorb them to the support surface before addition of the probe. In this case, hybridization takes place on the support surface. In either embodiment, the relatively long polynucleotides bind to the support through interaction between the cationic surface of the support with the negatively charged polynucleotide backbone. Probe molecules not bound to polynucleotide are not bound to the support and remain in solution.

The support, and any nucleotide probe bound as a hybrid with the polynucleotide, can be separated from solution by decantation, centrifugation or filtration. If the particles are magnetic, magnetic field separation can be used. In purification procedures, the nucleotide multimer can be recovered from the solid support by use of elution techniques. In the case of probe assays, the presence of label in the solid phase or in solution can be determined and related to the presence and amount of target nucleic acid sequence contained within polynucleotides in the sample for qualitative and quantitative determinations of diagnostic significance.

In all embodiments of the invention, there is provided a highly selective method for separating nucleotide multimers from non-nucleotidic material and for separating mixtures of nucleotide multimers based on their relative lengths. Accordingly, a variety of purification and assay procedures, including qualitative and quantitative procedures, can be carried out according to the invention.

5. DETAILED DESCRIPTION OF THE INVENTION

The well-known technique of nucleic acid hybridization exploits the ability of single stranded nucleotide multimers to combine (hybridize) with complementary strands under appropriate conditions. This invention provides a method for detecting the presence of a polynucleotide which has formed a hybrid with a nucleotide probe. The invention also provides a method for purifying nucleotide multimers and hybrids thereof.

Any method for the purification of nucleotide multimers or hybridization of polynucleotides in clinical samples must overcome the difficulties posed by biological contaminants which may interfere with separation as well as promote degradation of polynucleotides. In the case of ribosomal RNA ("rRNA"), for example, purification requires the removal of various proteins from the rRNA with which the rRNA is normally complexed. In addition, various nucleases and other enzymes must be inactivated to prevent degradation of the rRNA.

Hybridization normally involves a long target polynucleotide molecule, i.e., a single stranded DNA or RNA consisting of about 100 or more nucleotides (bases). To determine the presence or absence of a particular base sequence (target sequence) within the targeted DNA or RNA, nucleotide probe molecules are synthesized chemically or isolated from biological DNA or RNA through a variety of methods known in the art. The nucleotide probes are complementary to the desired base sequence of the target and are normally labeled with a detectable chemical species. However, the labeling of the nucleotide probe is not absolutely necessary if the hybrid can be detected by other means. Typically, probes are oligonucleotides of from 15–50 bases long, though they may be up to several hundred bases in length. When the target base sequence is present, the nucleotide probe binds to the target through base pairing interactions. Once hybridization is complete, the hybrid is usually separated from the solution which contains unhybridized nucleotide probe molecules. However, in some applications it may be sufficient to merely segregate the soluble and insoluble phases, for example, by centrifugation or other techniques which concentrate immobilized hybrid without removing the support from the medium from which the polynucleotide hybrid has been adsorbed. Once the hybrid is segregated or separated free of unhybridized probe, the hybrid is detected by standard methods. Direct labeling methods include radioisotopes, enzymes, fluorescent and chemiluminescent molecules. Indirect labels are also known wherein a chemical species, which is not detectable in and of itself, can be detected when it binds to another complex. An example of indirect labeling is the detection of biotin-labels employing conjugates between streptavidin and enzymes.

Other means of detection which do not require a labeled nucleotide probe could employ intercalators unique to the hybrid, antibodies specific for the hybrid, sensitive gravimetric means, changes in the reflectance of electromagnetic energy, or methods which would permit electronic detection. Of course, in certain cases, it may be desirable to measure unhybridized probe and such procedures are also within the scope of this invention.

When cationic solid supports and appropriate separation solutions are used according to the method of this invention, polynucleotide target molecules bind to the support but unbound nucleotide probes do not bind the support significantly. The precise theoretical explanation of this phenomenon is not entirely clear and the inventors do not wish to be bound to any particular theory, but it is undoubtedly related to charge-charge interactions and the density of cations on the surface of the support. One possible mechanism is that under moderate buffer conditions multiple charged regions of a long polynucleotide cooperatively help bind each other the surface of the cationic solid support. In contrast, shorter nucleotide probes do not possess the same multiplicity of charge-charge binding regions and may thus be less strongly bound to the support. Regardless, the ability of these supports to selectively bind long polynucleotides over oligonucleotides or polynucleotides is clear. This is shown in the examples which follow and points out the particular suitability of the method of this invention for the purification and separation of various polynucleotide mixtures. Unlike the prior art techniques, the method of the invention permits rapid separation of nucleotide multimers on the basis of their length and charge, most notably in hybridization procedures.

It is also within the scope of this invention to use as probes analogues of conventional DNA or RNA which have a lower negative charge in the phosphate backbone. Among such analogues may be mentioned the methyl phosphonates described in Miller et al., *Biochemistry*, 25, 5092 [1986].

Some suggestions have been made regarding the use of a nucleotide probe covalently bound to magnetic microspheres to select for a complementary nucleotide strand in solution. But it is known in the art that the covalent bonding of nucleotide multimers directly to solid supports may create steric conditions which are unfavorable for the proper interaction between complementary strands necessary for hybridization. (See, Life Technologies, "Immobilization of Nucleic Acids" WO 85/04674 [Oct. 24, 1985]). In the absence of a detailed disclosure in this regard, the method described by Whitehead is inappropriate for purification and hybridization. The present invention, circumvents the need for covalent bonding by relying on ionic interactions to effect the separation. Therefore, in a particularly preferred embodiment of the invention, magnetic microspheres bearing a polycationic surface are used to remove nucleotide multimers and hybrids thereof, from solution in any of the various procedures described above.

The methods of the current invention employ two main elements. These are the cationic solid supports and one or more of several contacting solutions employed to facilitate immobilization, separation, washing, and elution steps related to procedures for purifying nucleotide multimers and for assaying for target sequences in polynucleotides based on formation of hybrids with nucleotide probes. These solutions are used for immobilizing polynucleotides, separating polynucleotide hybrids and nucleotide probes, washing immobilized polynucleotides (including hybrids between polynucleotides and nucleotide probes), eluting immobilized polynucleotides, (including hybrids between polynucleotides and nucleotide probes), or eluting a detectable element which correlates with the presence of the immobilized hybrid between polynucleotides and nucleotide probes.

An interplay exists between the composition of the cationic solid support and the formulation of the contacting solution such that the composition of the contacting solution is determined in part by the composition of the cationic solid support and vice versa.

Furthermore, there is a close interplay between many of the contacting solutions since the components of one such solution may be carried over and modified by adding reagents in order to generate the composition needed in the next step of the method.

In order to clarify the uses of these formulations they can, in general, be broken down into three areas of use. These are:

I. Purification of polynucleotides or nucleotide multimers.

II. Immobilization of polynucleotide followed by hybridization typically to test for unique nucleotide sequences contained within said polynucleotides.

III. The separation from, and detection of, hybrids between polynucleotides and nucleotide probes preformed in solution.

Depending upon which of these procedures one wishes to carry out, a different set of contacting solutions may be required. In general, the steps and solutions useful for each of these procedures, although one or more steps and the use of one or more solutions may not be necessary in every case, is as follows:

I. Purification of Nucleotide Multimers (1) Immobilization of the nucleotide multimer, usually a polynucleotide, on the cationic solid support in the presence of a SEPARATION SOLUTION.

(2) Removal of contaminants employing a WASH SOLUTION and separation of the immobilized multimer on the cationic solid support and the solution phase.

(3) Recovery of the multimer from the surface of the cationic solid support using an ELUTION SOLUTION.

II. Immobilization of Polynucleotides Followed By Hybridization (1) Immobilization of the polynucleotide on the cationic solid support in the presence of a SEPARATION SOLUTION.

(2) Removal of contaminants employing a WASH SOLUTION (optional).

(3) Contacting the immobilized polynucleotide with a nucleotide probe in a HYBRIDIZATION SOLUTION designed to minimize immobilization of unhybridized nucleotide probe.

(4) Removal of unhybridized probe using a WASH SOLUTION which minimizes immobilization of unhybridized nucleotide probe and separation of the immobilized hybrid on the cationic support and in the solution phase (optional).

(5) Recovery of the hybrid or a detectable element which correlates with the presence of the immobilized hybrid using an ELUTION SOLUTION (optional).

(6) Detecting the hybrid or a detectable element associated with the hybrid which correlates with the presence of the hybrid, or the unhybridized nucleotide probe.

III. Separation and Detection of Hybrids Formed in Solution (1) Hybridization in the presence of a HYBRIDIZATION SOLUTION between a nucleotide probe and a polynucleotide which contains a base sequence complementary to the nucleotide probe.

(2) Contacting the hybridization mixture with a cationic solid support and a SEPARATION SOLUTION so as to permit any hybrids formed to bind the cationic solid support without permitting significant immobilization of the unhybridized nucleotide probe.

(3) Removal of unhybridized probe using a WASH SOLUTION which minimizes immobilization of unhybridized nucleotide probe (optional).

(4) Recovery of the hybrid or a detectable element which correlates with the presence of the immobilized hybrid using an ELUTION SOLUTION (optional).

(5) Detecting the hybrid or a detectable element which correlates with the presence of the hybrid or the unhybridized nucleotide probe in step (3).

As those skilled in the art will recognize, this polycationic support can be used in a variety of assay formats, including direct binding, competition and probe displacement assays. In addition, the labels may be either direct or indirect labels. In some probe displacement assay formats, hybridization could cause label to appear in the unbound, as opposed to the bound phase. The examples above serve solely to illustrate one characteristic of the cationic support to discriminate nucleotid multimers. This invention is not to be limited to any particular assay format.

For clarity the further description of this invention will be broken down into the elements relating to the composition of cationic solid support and the formulations of various contacting solutions. However, those skilled in the art will appreciate that actual practice of the invention will be preceded by steps such as sample collection and sample treatment to liberate the nucleotide multimers being purified or probed. For example, the necessity to perform cell lysis and procedures for doing so are well known to the art and a description of such procedures are unnecessary to a complete description of the invention.

CATIONIC SOLID SUPPORTS

The polycationic support matrix of this invention can be selected from a wide variety of inorganic and organic materials including but not limited to metal oxides, glasses, polyamides, polyesters, polyolefins, polysaccharides, polyglycols, and polyaminoacids. The principle requirement is that the matrix support does not unduly adsorb either contaminants or nucleotide probes under the conditions being employed.

Preferred supports are those with a high surface to volume ratio in order to minimize the amount of material needed. Such ratios can be achieved by using particles, particularly micron sized particles, highly porous materials, such as agarose, or small diameter fibers arranged either singly or into a filter mat. The use of small, micron sized particles are preferred.

In the examples which follow, it has been shown that the matrix can comprise a magnetically responsive iron oxide as described by Whitehead, et al. (U.S. Pat. No. 4,554,088; Nov. 19, 1985), a latex microsphere, a sepharose bead, or a suitably functionalized membrane, though the invention is not limited to these materials.

The support should have a cationically modified surface of sufficient charge density to enable the adsorption of the desired polynucleotide under appropriate conditions of salt, detergent and temperature. The charge density may need to be determined empirically but generally is in the range of 0.01–10 micro equivalents per milligram of support.

The charges may be introduced by a range of cations including but not limited to alkyl and aryl amines including primary amines, secondary amines, tertiary amines, quaternary amines, as well as guanidines and imines.

Examples of such moieties include 3-aminopropyl groups, 2-aminoethyl-3-aminopropyl groups, tris (2-aminoethyl) amine, spermine, spermidine, pentamethyl-2-aminoethyl-3-aminopropyl groups, and polymers with amine functionalities such as polylysine, polyarginine, polyethylenimine, and polyallylamine.

Functionalities commonly present on the surface of the supports can be readily modified with reagents containing cationic functionalities. Numerous procedures are known in the art for introducing functional groups onto the surface of almost any matrix. See for example, Porath and Axen (Methods in *Enzymology*, 44, 19–45. [1976]), and Goldman et al. (in "Biochemical Aspects of Reactions on Solid Supports", G. R. Stark, ed., Academic Press [1971]).

In part the formulation of the cationic support is determined empirically depending upon its use. A typical protocol for formulating the solid support follows, but other similar procedures can also be used. If the cationic solid support is to be used solely for the purification of nucleotide multimers, target multimers are tested for their ability to bind to the support in buffers which are less than 0.6M sodium phosphate, pH=6.8, and for their ability to be eluted in greater than 20 mM sodium phosphate, pH=6.8. If the polynucleotide does not bind in less than 0.6M sodium phosphate, pH=6.8 the cation density is increased or the multiplicity of cations at single attachment sites is increased. (For example, replacing a 3-aminopropyl group with a tris (2-aminoethyl) amine.) On the other hand if the polynucleotide can not be eluted in buffers greater than 20 mM sodium phosphate, pH=6.8, the cation density is reduced or the multiplicity of cations at single attachment sites is reduced.

When the support is to be used for separating polynucleotide hybrids from nucleotide probes, there is the additional requirement that the nucleotide probe not be significantly bound under conditions which retain the hybrid. These conditions can be tested by monitoring the binding of both the polynucleotide and the nucleotide probe between 20 mM and 0.6M sodium phosphate, pH=6.8, and selecting a buffer concentration which gives a maximum binding ratio of polynucleotide to nucleotide probe. If satisfactory binding ratios cannot be achieved, the surface density and multiplicity of cations is further modified.

It should be noted that generally the length of the polynucleotide to the nucleotide probe should usually be in the ratio of greater than 3 to 1 for good separation, and is preferably greater than 5 to 1. However, the use of DNA or RNA analogues having lower negative charge in the probe backbone can permit relaxation of this criterion. In the case of some probe displacement and competition assays, however, the 3 to 1 ratio need not be met and, in fact probe constructions may be longer than the target.

CONTACTING SOLUTIONS

In addition to the polycationic support, the separation solution is of particular importance and should be carefully designed to facilitate immobilization and to prevent degradation of the nucleotide multimers and their probe hybrids. The contacting solutions can include various buffers, the concentrations of which will vary depending upon the operation desired. The components of the solution and their concentrations of the solution are dependent upon a number of factors: the need, if any, to inactivate nucleases, especially in clinical samples; the polynucleotide separation desired; and other steps desired after separation. If, for example, a subsequent enzyme detection scheme is to be included, protein denaturants or inhibitors may be necessary as part of the separation solution in order to maximally reduce background from endogeneous enzyme activity.

The components which remain from previous procedural steps must also be considered. For example, in most cases separations will be done by removing polynucleotides from biological material or hybridization reactions. Various components and reagents which are used either to liberate said polynucleotides from biological samples or are used to facilitate hybridization (i.e., accelerated rate hybridization) will remain as components of the subsequent separation solution.

The contacting solutions have many components in common and in some cases their compositions may be identical. For example, the composition of the wash solution and the separation solutions may be similar in regard to inhibiting nuclease activity, preventing the binding of nucleotide probes, and in negating adverse affects of substances associated with hybridization rate acceleration.

The first step in formulating the contacting solutions is dependent upon the desired use of the cationic solid support. The next step is to formulate the contacting solutions. In general the reagents for formulation are selected from the following categories.

ENZYMES—These are used in part to degrade and inhibit nucleases, disrupt protein/nucleic acid interactions, and in some cases cleave label which is associated with immobilized hybrids. They may include proteases, diesterases, nucleases and peptidases.

NUCLEASE INHIBITORS—These agents are employed to prevent degradation of both polynucleotide molecules and nucleotide probes. They include ribonuclease inhibitors such as vanadyl sulfate, vanadyl ribosides and RNAGuard™ (human placental ribonuclease inhibitor, Pharmacia Fine Chemicals, Piscataway, N.J., USA), deoxyribonuclease inhibitors, and detergents such as sodium dodecylsulfate and lithium lauryl sulfate which are general protein denaturants.

CHELATING AGENTS—These substances are utilized to chelate various metals which when unchelated are essential for the activity of various enzymes. For example, many deoxyribonucleases require $Ca^{2+}$ for activity. Chelation of metals ions is also important for optimizing hybridization reactions since metals such as $Mn^{2+}$ can interfere with hybridization. Chelating agents include ethylene diaminetetracetic acid (EDTA) and ethylene glycol bis (2-aminoethyl ether)-N, N,N',N'-tetracetic acid (EGTA).

DETERGENTS—These substances are used to help solubilize particulate material, inhibit nucleases, and reduce unwanted immobilization of contaminants and nucleotide probes to cationic solid support employing Separation Solutions and Wash Solutions. Detergents may also be used to accelerate hybridization reactions.[2] In some circumstances one detergent may be used to abolish the adverse effects of a second detergent by forming mixed micelles. Substances in the detergent category include sodium dodecyl sulfate, lithium lauryl sulfate, N-lauroylsarcosine, sodium diisobutyl sulfosuccinate, Triton® X-100, Brij®, Tween®-20 and Tween®-80.[3]

[2] Patent pending on accelerated rate system.
[3] Triton®, Brij®, and Tween® are registered trademarks of ICI Americas.

BUFFER SALTS—These substances are employed to maintain pH ranges which are compatible with nucleotide multimers stability, hybrid stability, and the stability of agents used as labels. These substances are also used to establish the primary balance between immobilization of hybrids on the cationic solid support and retention of nucleotide probes in solution using Separation Solutions. In addition, they are employed to establish the stringency in the Hybridization Solutions. The concentration of various salts can also be used to assist the elution of hybrids or a nucleotide probe associated with a hybrid from the surface of the support. Such substances may include salts of potassium, sodium, calcium, guanidine, chloride, fluoride, sulfate, phosphate, acetate, succinate, physic acid, and tripolyphosphate.

ORGANIC SOLVENTS—These solutions are used to help emulsify various substances, alter hybridization temperatures and conditions, remove contaminating substances and assist in the removal of nucleotide probes and hybrids employing elution solutions. Such organic solvents may include methanol, ethanol, isopropylalcohol, formamide, and dimethyl formamide.

OTHER ORGANIC AND INORGANIC SUBSTANCES—Other substances may be used in various contacting solutions in order to impart a desired property. These include organic and inorganic acids such as acetic acid, phosphoric acid, hydrogen fluoride, sulfuric acid, and nitric acid. They also include inorganic substances which might be used to remove the label from a nucleotide probe employing an elution solution. These may include periodate, lead acetate and manganese dioxide.

The individual contacting solutions which may be used in specific cases are generally formulated as follows:

HYBRIDIZATION SOLUTION—Formulated generally with a salt buffer, detergents, nuclease inhibitors and chelating agents. The formulation is compounded to facilitate hybridization between a polynucleotide and nucleotide probe. Furthermore, when the polynucleotide is immobilized prior to hybridization the formulation is selected to preclude significant binding of the nucleotide probe to the cationic support.

SEPARATION SOLUTION—Comprises generally a salt buffer, detergents, and nuclease inhibitors so as to permit immobilization of the hybrid without permitting the significant immobilization of the nucleotide probe.

WASH SOLUTION—Formulated generally with a salt buffer and detergents so as to keep the hybrid immobilized while permitting removal of contaminants and unhybridized nucleotide probe.

ELUTION SOLUTION—Comprises generally a salt buffer, organic solvents, detergents and other reagents so as to liberate a polynucleotide, polynucleotide hybrid, nucleotide probe, or a label associated with a hybrid from the surface of the support.

DETECTION SOLUTIONS—Formulated specifically to detect the hybrid or a specific label. Its composition is dependent on the detection means and is formulated according to prior art methods. For example, if the label is an enzyme, the detection solution will contain the selected enzyme substrate and other reagents.

Persons skilled in the art and having the benefit of the foregoing general description will be able to tailor the components of specific contacting solutions to a wide variety of procedures and conditions well within the skill of the art, particularly with reference to the following examples. Materials used in the following examples include: Magnetic amine microspheres were obtained from Advanced Magnetics, Inc. (Cambridge, Mass., USA; Biomag M4100, 50 mg/ml in water); lysozyme was Grade I from Sigma, St. Louis, Mo., USA; urea was enzyme grade from Bethesda Research Labs, Bethesda, Md., USA; RNAGuard™ (human placental ribonuclease inhibitor) from Pharmacia, Piscataway, N.J., USA; Cytoscint™ (liquid scintillation cocktail) from WestChem, San Diego, Calif., USA; polyethylene glycol 8000 from Eastman-Kodak, Rochester, N.Y., USA; diisobutyl sulfosuccinate (DIBSS), see Examples 7 and 12, used in Gen-Probe, Inc. accelerated rate system (Patent Pending), from Mona, Ind., USA; hydroxyapatite (HAP) and Zwittergent 3-14 were from Behring-Diagnostics, Calbiochem Division, La Jolla, Calif., USA; sodium dodecyl sulfate (SDS) was from Sigma, St. Louis, Mo., USA, as was Trizma-base (Tris); Triton X-100 was from Fisher Diagnostics, Orangeburg, N.Y., USA; stock [$^3$H]-rRNA (16S and 23S subunits of the E. coli ribosome). The rRNA of the 16S subunit is approximately 1500 bases long; the 23S subunit is approximately 3000 bases. All other reagents were reagent grade. All phosphate buffers (PB) were the sodium salt, pH 6.8 unless otherwise stated. All manipulations were performed at room temperature in 1.5 ml screw-capped polypropylene microcentrifuge tubes unless otherwise stated.

EXAMPLE 1

The Binding of rRNA to Magnetic Amine Microspheres

To determine the effects of various buffer concentrations on rRNA binding, mixtures for separation were prepared by combining 5 µl of magnetic amine microspheres, 1 µl (1 µg) of [$^3$H]-rRNA and 100 or 150 µl of the reagents listed below in Table 1. The reagents include those which would be used in a complete assay protocol and were studied to determine their affect on rRNA binding. The mixtures were vortexed lightly for 2 seconds and allowed to stand for 5–10 minutes. The magnetic amine microspheres were magnetically pelleted using a BioMag Separator (Advanced Magnetics, Inc. catalog #M4101) to the bottom of the tube and the supernatants (non-bind) were removed. The magnetic amine microspheres were then washed (once or twice) by vortexing them for 1–2 seconds in 100 or 150 µl of the buffer in which binding had taken place, magnetically pelleting the magnetic amine microspheres and removing the supernatants. The magnetic amine microspheres were then resuspended in 100 or 150 µl of wash buffer and added to 15 ml of Cytoscint in 20 ml polypropylene tubes as were the non-bind and wash fractions. The amount of tritium in each sample was then determined using a Nuclear Chicago scintillation counter.

As shown in Table 1 below, the removal of rRNA by adsorption to magnetic amine microspheres is sensitive to changes in buffer concentration but is not unduly affected by other reagents that would be present in a complete assay protocol. More importantly, the effects of reagents that do decrease binding can be manipulated by varying their concentrations or by adding other reagents into the solution.

TABLE 1

| Reagent System | % [$^3$H]-rRNA Bound to Microspheres |
| --- | --- |
| H$_2$O | 94 |
| 50 mM PB | 99 |
| 100 mM PB | 98 |
| 140 mM PB | 92 |
| 200 mM PB | 89 |
| 300 mM PB | 14 |
| 1M NaCl | 99 |
| 1M NaCl + 50 mM PB | 95 |
| Tris, PEG[4/] | 99 |
| Sucrose, Lysozyme[5/] | 99 |
| 8M urea | 74 |
| 4M urea | 97 |
| 1% Triton X-100 | 100 |
| 5% Triton X-100 | 47 |
| 1% Zwittergent 3-14 | 98 |
| 5% Zwittergent 3-14 | 78 |
| 2M urea + 1M LiCl | 73 |
| 10 mM EDTA in 50 mM PB | 86 |
| 500 U/ml RNAGuard ™ | 100 |
| 67% HOAc | 37 |
| 50% HOAc | 75 |
| 33% HOAc | 79 |
| 20% HOAc | 99 |
| pH 4 NaOAc[6/] | 95 |
| 18% DIBSS[7/] | 25 |
| 18% DIBSS, 50 mM PB | 35 |
| 184 DIBSS, 5% Triton X-100, 50 mM PB | 90 |
| 18% DIBSS, 1% SDS, 5% Triton X-100, 50 mM PB | 80 |

[4/]0.1M Tris (pH 7.5), 1M NaCl, 2.5% polyethyleneglycol.
[5/]7% sucrose, 0.08M glycine (pH 9.0 w/NaOH), 8 mM EDTA, 25 mM DTT, 2 mg/ml lysozyme.

EXAMPLE 2

The Binding of DNA to Magnetic Amine Microspheres

This study was designed to determine the effects of different buffer concentrations and other assay reagents on DNA binding to magnetic amine microspheres. The method of Example 1 was used, except [$^3$H]-cDNA against rRNA from Mycoplasma pneumonia was used instead of stoct rRNA. The cDNA was a mixture of cDNAs ranging in size from approximately 400 to 1600 bases.

As shown in Table 2, cDNA binds to magnetic amine microspheres about as well as rRNA and the extent of binding can be manipulated by variations in buffer concentrations as well as the addition of other reagents.

TABLE 2

| Reagent System | % [$^3$H]-rRNA Bound to Microspheres |
| --- | --- |
| H$_2$O | 100 |
| 0.05M PB | 100 |
| 0.10M PB | 99 |
| 0.15M PB | 99 |
| 18% DIBSS, 5% Triton X-100, 100 mM PB | 0 |
| 14.5% DIBSS, 3.75% Triton X-100, 75 mM PB | 0 |
| 9% DIBSS, 2.5% Triton X-100, 50 mM PB | 89 |
| 4% DIBSS, 5% Triton X-100, 50 mM PB | 100 |

[6/]HOAc adjusted to pH 4 w/5N NaOH. Final HOAc conc = 44%.
[7/]wt: vol diisobutyl sulfosuccinate.

EXAMPLE 3

The Elution and Hybridization of rRNA from Magnetic Amine Microspheres

In this experiment, [$^3$H]-rRNA was eluted from magnetic amine microspheres and hybridized. In addition to the materials described in Example 1, [$^{32}$P]-ATP was obtained from Amersham Corp., Arlington Hts., Ill., USA, and T4 polynucleotide kinase from Bethesda Research Labs, Inc., Gaithersburg, Md., USA.

A probe was synthesized using an Applied Biosystems, Inc. Model 380A DNA Synthesizer. A deoxyoligonucleotide was produced with the sequence "5'-AGGACCGTTATAGT-TAGGGCCGCCGT-3'" using standard phosphoramidite chemistry (this sequence is complementary to the bases 1901–1926 of the 23S subunit of the *E. coli* ribosome) (Patent pending on probe sequence.) The oligomer was then labeled on the 5' end using [$^{32}$P]-ATP and T4 polynucleotide kinase according to the procedure of Maxam and Gilbert (*Proc. Natl. Acad. Sci. U.S.A.*, 74, 560 (1977)).

[$^3$H]-rRNA immobilization, elution and hybridization: [$^3$H]-rRNA was immobilized by combining 10 µl of magnetic amine microspheres (50 mg/ml), 100 µl of 0.14M PB and 3 µl of [$^3$H]-rRNA (1 mg/ml). The mixture was lightly vortexed 1–2 seconds and allowed to stand 5–10 minutes. The magnetic amine microspheres were magnetically pelleted and the supernatant (non-bind) was removed. The magnetic amine microspheres were then washed one time with 100 µl of 0.14M PB and the supernatant removed.

In order to elute the [$^3$H]-rRNA, 50 µl of 0.6M PB were added to the magnetic amine microspheres and the mixture was vortexed 1–2 seconds. Five microliters were removed and counted for radioactivity (See Example 1). The remainder of the solution was allowed to stand for 15–30 minutes at room temperature. The magnetic amine microspheres were then magnetically pelleted and a 5 µl aliquot of the supernatant was counted for radioactivity. Another aliquot of the supernatant was removed and placed in the following hybridization mixture: 25 µl eluted [$^3$H]-rRNA in 0.6M PB (1.1 pmol), 0.5 µl [$^{32}$P]-DNA probe (0.23 pmol), 1.5 µl 1% SDS, and 4 µl H$_2$O totaling 31 µl of solution.

A control hybridization was also performed using the same amount (based on radioactivity) of stock [$^3$H]-rRNA: 1.8 µl stock [$^3$H]-rRNA (1.1 pmol), 0.5 µl [$^{32}$P]-DNA probe (0.23 pmol), 14.8 µl 1.0M PB, 1.5 µl 1% SDS, and 12.4 µl H$_2$O totaling 31 µl of solution.

The hybridization mixtures were then incubated for 3 hours at 50° C. Each mixture was added to 5 ml of 0.14M PB containing 2% hydroxyapatite (HAP) in a 7 ml polypropylene scintillation vial. After vortexing for 15 seconds the samples were incubated for 5 minutes at 50° C. The HAP was then pelleted by centrifugation for 2 minutes in an IEC table top clinical centrifuge (Needham Hts., Mass., USA) at 2000×G. The supernatant was removed, 5 ml of 0.14M PB added and the mixture vortexed 15 seconds, followed by centrifugation as described above. The supernatant was removed and the HAP, non-bind and wash solutions were counted for Cerenkov [$^{32}$P] activity in order to determine percent hybridization, i.e., the percent of the probe associated [32P] counts bound to the HAP.

Of the [$^3$H]-rRNA bound to the support, 80% eluted. Reaction of either eluted rRNA or stock rRNA with the DNA probe yielded 31% hybridization. The results indicate that purification of polynucleotides by the method of the invention does not damage them for further hybridization and other studies.

EXAMPLE 4

The Binding of rRNA in Urine to Magnetic Amine Microspheres

This experiment was undertaken to determine the effect of urine on rRNA binding to magnetic amine microspheres. In addition to the materials described in Example 3, fresh urine samples were obtained from volunteers.

To 100 μl fresh urine was added 200 μl of 50mM PB, 8M urea or HOAc, pH 4 (glacial acetic acid was adjusted to pH 4 with the addition of 0.28 ml of 10N NaOH per ml of HOAc) as well as 1 μl stock [$^3$H]-rRNA (1 μg) and 5 μl magnetic amine microspheres. The mixtures were worked up as described in Example 1, except that each was washed with 200 μl of 50 mM PB.

The results showed that in the presence of urine, the urea, which is used with biological samples to free nucleic acids and denature proteins and nucleases, decreases the binding of [$^3$H]-rRNA to 0.8%. In urine plus phosphate buffer alone, only 13% of the [$^3$H]-rRNA bound to the support. Only in combination with HOAc, pH 4 did 100% of the rRNA bind to the magnetic amine microspheres.

EXAMPLE 5

The Binding of rRNA Suspended in Sputum to Magnetic Amine Microspheres

This study was undertaken to determine the proper combinations and concentrations of buffers and reagents necessary to bind [$^3$H]-rRNA in more complex biological samples. The materials described in Example 4 plus pooled, frozen sputa (each pool containing sputum from several patients) were obtained from various hospitals.

Sputum samples were first liquified (immediately before use) by adding 1/10 volume of 0.5M dithiothreitol (DTT), followed by vortexing and incubation for 10–15 minutes at 22° C. A variety of reagents were then added to 100 μl aliquots of the liquified sputum, along with 1 microliter stock [3H]-rRNA (1 μg) and 5 μl magnetic amine microspheres. After 5 minutes of incubation at 22° C., the samples were then processed as in Example 1 (with the exception that each was washed with 200 μl 50 mM PB) to determine the extent of [$^3$H]-rRNA binding. The results are summarized in Table 3.

TABLE 3

Reagent Systems for [$^3$H]-rRNA removal from Sputum with Magnetic Amine Microspheres

| Sample Composition | Final Concentrations HOAc[8/] | Urea | % [$^3$H]-rRNA Bound to Magnetic Amine Microspheres |
|---|---|---|---|
| 100 μl sputum + 100 μl HOAc + 300 μl 50 mM PB | 20% | — | 43 |
| 100 μl sputum + 100 μl HOAc | 50% | — | 8 |
| 100 μl sputum + 256 μl pH 4 HOAc | 56% | — | 41 |
| 100 μl sputum + 256 μl pH 4 HOAc + 150 μl 8M urea | 39% | 2.4M | 50 |
| 100 μl sputum + 300 μl HOAc/urea[9/] | 50% | 4.0M | 81 |

EXAMPLE 6

The Hybridization of rRNA Purified from Sputum

In this experiment, the [$^3$H]-rRNA removed from sputum and bound to the support was eluted and studied to determine whether the separation method used in the invention unduly decreases hybridizability.

A deoxynucleotide probe with the sequence "5'-GGC-CGTTACCCCACCTACTAGCTAAT-3'" (complementary to bases 235–260 of the 16S *E. coli* ribosome) 10/ was synthesized and labeled with [$^{32}$P] as described in Example 2.

10/ Patent pending on probe sequence.

After binding of [$^3$H]-rRNA in sputum to magnetic amine microspheres and removal of the non-bind fraction (see Example 5), the magnetic amine microspheres were washed one time with 1M NaCl, 50 mM PB. After removal of the supernatant, 50 μl of 0.6M PB were added and the mixture incubated 30 minutes at 22° C. or for 15 minutes at 72° C. with occasional mixing. The magnetic amine microspheres were then magnetically pelleted and the percent [$^3$H]-rRNA eluted was determined by comparison of the radioactivity of aliquot of the supernatant with an aliquot of the magnetic amine microspheres before incubation (see below).

The ability of the eluted [$^3$H]-rRNA to hybridize to a complementary DNA-probe (see Materials) was determined by comparing hybridizability of eluted rRNA with stock rRNA, both in target excess and probe excess. The following hybridization mixtures were prepared:

(1) 30 μl eluted rRNA in 0.6M PB (0.44 pmol), 1 μl DNA-probe (0.07 pmol), 4 μl 1% SDS, and 2.5 μl H$_2$O, totaling 37.5 μl.

(2) 0.7 μl stock rRNA (0.44 pmol), 29.3 μl 0.6M PB, 1 μl DNA-probe (0.07 pmol), 4 μl 1% SDS, and 1.6 μl H$_2$O totaling 36.6 μl.

(3) 9.35 μl eluted rRNA in 0.6M PB (0.14 pmol), 1 μl DNA-probe (0.7 pmol), and 1.34 μl 1% SDS totaling 11.69 μl.

(4) 0.22 μl stock rRNA (0.14 pmol), 9.13 μl 0.6M PB, 1 μl DNA-probe (0.7 pmol) and 1.06 μl 1% SDS totaling 11.41 μl.

The hybridization mixtures were then incubated for 2 hours at 50° C., followed by isolation of hybrids on HAP as described in Example 2. In target excess, eluted rRNA showed 67% hybridizability as compared to stock rRNA. In probe excess, eluted rRNA showed 65% hybridizability compared to stock rRNA.

EXAMPLE 7

The Recovery of RNA/DNA Hybrids from Buffer Solutions Using Magnetic Amine Microspheres This experiment was designed to study magnetic amine microspheres as a separation support for RNA/DNA hybrids formed in solution. The materials were the same as those described in Example 3. In addition, a Legionella specific DNA probe (average length 100 bases) was used.

The ability of magnetic amine microspheres to separate RNA/DNA hybrids was studied in two different systems.

System 1: An RNA/DNA hybrid was formed by combining 8 μl stock [$^3$H]-rRNA (5 pmol), 1 μl deoxyoligonucleotide probe (0.5 pmol), 10 μl 0.28M PB and 1 μl 1% SDS, and incubating this mixture for 1.5 hours at 50° C. Additionally, a control mixture was made exactly as the hybrid mixture, except that the 8 μl of target RNA was replaced with 8 μl of water. This control mixture was also incubated for 1.5 hours at 50° C. Half of each mixture (10 μl) was added to 5 ml of 2% HAP in 0.14M PB and worked up as described in Example 2. The other half of each mixture was added to 200 μl 0.14M PB+10 μl magnetic amine microspheres and worked up as described in Example 1 (using 0.14M PB for washing).

System 2: An RNA/DNA hybrid mixture was made by combining 4 μl Legionella rRNA (2.5 fmol), 2 μl Legionella probe (1.3 fmol) and 196 μl containing 44% DIBSS, 30mM PB and 3% SDS. A control mixture was made exactly as the hybrid mixture, except that the 4 μl of target RNA was replaced with 4 μl of water. Both mixtures were incubated for 2 hours at 72° C. A 50 μl aliquot of each mixture was added to 5 ml of 2% HAP in 0.14M PB and worked up as described in Example 2, except at 72° C. and two washes. Another 50 μl of each mixture was added to a separation mixture such that the final conditions were 150 μl total volume, containing 18% DIBSS, 5% Triton X-100, 0.1M PB and 10 μl magnetic amine microspheres. The magnetic amine microspheres were then worked up as described in Example 1, except at 72° C. and two washes (wash 1 was 18% DIBSS, 5% Triton and 0.1M PB; wash 2 was 5% Triton, 0.1M PB). The results are shown in Table 4.

TABLE 4

| Method of Separation | % Bound | | | |
|---|---|---|---|---|
| | System 1 | | System 2 | |
| | Hybrid | Control | Hybrid | Control |
| HAP | 53 | 1.5 | 30.3 | 0.4 |
| Magnetic Amine Microspheres | 51 | 0.5 | 28.6 | 0.2 |

This result indicates that the magnetic amine microspheres are capable of recovering RNA/DNA hybrids from buffer solutions, while leaving unhybridized probe in solution.

EXAMPLE 8

The Recovery of DNA/DNA Hybrids from Solution Using Magnetic Amine Microspheres

This experiment was undertaken to study magnetic microspheres as a separation support for DNA/DNA hybrids formed in solution. In addition to the materials described in Example 2, a synthetic 36-base deoxyoligonucleotide probe complementary to a 36-base region of the cDNA described in Example 2 was used.

The oligonucleotide was labeled with [$^{32}$P] as described in Example 3. A DNA/DNA hybrid mixture was made by combining 20 μl cDNA target (approximately 20 fmol), 1 μl DNA probe (approximately 60 fmol) and 200 μl containing 44% DIBSS, 30mM PB and 3% SDS. A control mixture was made exactly as the hybrid mixture, except that the 20 μl of target was replaced with 20 μl of water. Both mixtures were incubated for 2 hours at 60° C. A 50 μl aliquot of each mixture was added to either 450 μl of 2% HAP in 0.08M PB or 450 μl of 5% Triton, 45 mM PB plus 10 μl of magnetic amine microspheres. Each separation mixture was incubated at room temperature for 5 minutes, the HAP or the microspheres were pelleted as described in previous examples and the supernatants were removed. The pellets were washed one time at room temperature with 500 μl of either 0.08M PB (HAP) or 5% Triton, 45 mM PB (microspheres) as described in previous examples. All fractions were then dissolved in 15 ml Cytoscint and counted for radioactivity as described previously. The results in Table 5 compare favorably with those for System 2 in Example 7 indicating that binding of hybrids is charge dependent and unaffecting by whether the target is RNA or DNA.

TABLE 5

| Method of Separation | % Bound | | Net % Hybridization |
|---|---|---|---|
| | Hybrid | Control | |
| HAP | 33.9 | 1.1 | 32.8 |
| Magnetic Amine Microspheres | 36.1 | 4.4 | 31.7 |

EXAMPLE 9

Study of Elution Buffers for Removal of Labeled Nucleotide Probes Associated with Nucleic Acid Hybrids Bound to Magnetic Amine Microspheres The potential of various elution buffers for removal of labeled nucleotide probes associated with DNA/RNA hybrids bound to magnetic amine microspheres was demonstrated by the following methods.

Method 1: A [$^{125}$I]-labeled deoxyoligonucleotide probe (prepared by standard methods) was hybridized to target RNA in 0.5M PB, pH 5 (30 minutes at 60° C., 30 μl total volume). Then, 1 ml of 0.25M PB, pH 5, 0.05% Triton X-100 and 2.5 mg magnetic amine microspheres was added, vortexed, and incubated 5 minutes at 60° C. The spheres were washed 2 times with 0.25M PB, pH 5, 0.05% Triton X-100. Potential elution agents were tested by adding 100 μl to aliquots (5%) of the magnetic amine microspheres, incubating 5 minutes at 60° C., separating supernatant from spheres and measuring the amount of [$^{125}$I] present in each fraction using a gamma counter (Iso-Data, Palatine, Ill., USA, Model 20/20DM). Results are summarized in Table 6.

TABLE 6

| Elution Agent | Percent Eluted |
|---|---|
| 0.25M PB, pH 5, 0.01% SDS, 50% formamide | 95 |
| 3M NsOAC, pH 5 | 95 |
| 0.25M PB, pH 5, 0.01% SDS, 50% DMSO | 85 |

TABLE 6-continued

| Elution Agent | Percent Eluted |
| --- | --- |
| 0.1M NaOAc, pH 5, 14 SDS, 1M Guanidinium-HCl | 70 |
| 0.1M NaOAc, pH 5, 1% SDS, 1M sodium propianate | 68 |
| 0.1M NaOAc, pH 5, 0.01% SDS, 0.1M sodium pyrophosphate | 65 |
| 1M sodium citrate, pH 5 | 60 |
| 0.25M PB, pH 5, 5% SDS | 56 |
| 0.1M NaOAc, pH 5, 1% SDS, 0.1M MgCl$_2$ | 40 |

These results demonstrate that a wide range of reagents are capable of removing labeled nucleotide probes from RNA/DNA hybrids bound to microspheres.

Method 2: To demonstrate that other elution reagents are capable of removing labeled nucleotide probes associated with DNA/RNA hybrids bound to amine magnetic microspheres, the following protocol was used to test these potential elution reagents.

A [$^{32}$P]-labeled deoxyoligonucleotide probe (prepared as described, supra) was hybridized to target rRNA in 0.48M PB (pH 5)/0.1% SDS (total volume 150 µl) for 30 minutes at 60° C. Then, 1 ml of 0.15M PB (pH 6.8)/5.0% Triton X-100 and 2.5 mg of amine magnetic microspheres was added, vortexed and incubated 5 minutes at 60° C. The microspheres were washed three times with 0.3M PB (pH 6.8). Elution reagents were then tested by adding 300 µl of the elution solution to the amine magnetic microspheres, incubating 5 minutes at 60° C., separating supernatant from spheres and measuring the amount of [$^{32}$P] present in each fraction using a scintillation counter (Delta 300 Scintillation System, Searle Analytical, Inc., Des Plaines, Ill., USA). Results are summarized in Table 7.

TABLE 7

| Elution Agent | Percent Eluted |
| --- | --- |
| 0.05M Phytic Acid, pH 8.0 | 91% |
| 0.05M Tripolyphosphate, pH 8.0 | 87% |
| 0.3M PB (pH 6.8)/50% formamide | 86% |

These results demonstrate that polyphosphates can efficiently elute nucleic acids from magnetic amine microspheres.

EXAMPLE 10

Use of Magnetic Amine Microspheres as a solid Phase Hybridization Support

In this experiment, target rRNA was bound to magnetic amine microspheres and then hybridized. To 5 µl of magnetic amine microspheres were added 100 µl 0.14M PB and 2 µl stock [$^3$H]-rRNA (2 µg, 1.26 pmol). The materials were the same as those described in Example 3. The mixture was incubated 10 minutes at 22° C., the magnetic amine microspheres magnetically pelleted and the supernatant removed. To the magnetic amine microspheres were added 20 µl 0.14M PB and 0.5 µl probe (0.23 pmol). As a control, hybrids were formed in a solution of 2 µl stock [$^3$H]-rRNA, 0.5 µl probe, 5 µl 0.28M PB, 0.5 µl 1% SDS and 2 µl H$_2$O. Both hybridization mixes were then incubated 3 hours at 40° C. The magnetic amine microspheres were washed 3 times with 100 µl 0.14M PB as described in Example 1. The results show the extent of hybridization of probe was 5% in the case of immobilized rRNA as compared with 20% for hybridization in solution (control).

EXAMPLE 11

Use of Magnetic Amine Microspheres to Purify Nucleic Acids from Cell Lysate

This experiment was undertaken to show that the magnetic amine microspheres described, supra, can be used to purify RNA from a crude sample without significantly reducing hybridizability. The method of purifying rRNA was studied using rRNA from Legionella pneumophilia. The materials were the same as those described in Example 5. In addition, a Legionella specific probe and Legionella pneumophilia organisms were obtained. San Diego, Calif., USA.

Cell lysis and release of rRNA was achieved by combining 30 µl water, 5 µl Legionella pneumophila suspension (5×10$^5$ organisms) and 5 µl 24% SDS, 0.08M Tris-base, 0.08M EGTA and 0.08M EDTA, followed by incubation for 30 minutes at 72° C. One quarter of the sample (10 µl) was then assayed directly for rRNA using the following assay mixture: 10 µl sample+114 µl 5.94M PB+1 µl DNA-probe[11]/ +75 µl water. The mixture was incubated 30 minutes at 72° C. and was then analyzed for hybrid formation using HAP as described in Example 2, except the HAP binding step was done at 72° C. instead of 50° C. To another 10 µl of sample was added 30 µl HOAc/urea (see Example 5), the mixture was vortexed 5 seconds, 5 µl of magnetic amine microspheres were added and the mixture was lightly vortexed (about 3 seconds). After incubating 5 minutes at 22° C. and subsequent washing with 150 µl 1M NaCl, 50mM PB at 22° C., the bound rRNA was eluted with 50 µl 0.6M PB (details described in Example 2). The eluant was then assayed for rRNA by combining 50 µl sample, 109 µl 5.94M PB, 1 µl DNA-probe and 40 µl water, incubating the mixture for 30 minutes at 72° C., and analyzing hybrid formation using HAP (see Example 2). Results are summarized in Table 8.

[11]/ Patent pending on accelerated rate system.

TABLE 8

| | % Hybridization |
| --- | --- |
| Direct Assay | 30 |
| Microsphere purification, elution, assay | 21 |

EXAMPLE 12

Purification of Nucleic Acids from Sputum with Magnetic Amine Microspheres

In this experiment, the use of magnetic amine microspheres for the purification of Legionella pneumophilia rRNA from sputum and subsequent hybridizability of said rRNA was demonstrated. The materials were the same as those in Example 7. A pooled sputum sample was liquified as described in Example 5. To 30 µl aliquots of this sputum sample or 30 µl aliquots of water were added 5 µl of a Legionella pneumophila suspension (2×10$^6$, 2×10$^5$ or 2×10$^4$ cells per 5 µl ). Using the same procedure as described in Example 11, the cells were lysed, one half of each sample was hybridized directly (20 µl sample and 65 µl water used here) and one half was hybridized after purification of the rRNA using magnetic amine microspheres (20 µl sample and 60 µl HOAc/urea used here). Hybrid formation was analyzed using HAP (see Example 2). The results are shown in Table 9.

TABLE 9

| | | % Hybridization |
|---|---|---|
| Water | 10⁶ organisms | 42 |
| | 10⁵ organisms | 33 |
| | 10⁴ organisms | 5.9 |
| Sputum | 10⁶ organisms | 67 |
| | 10⁵ organisms | 13 |
| | 10⁴ organisms | 2.6 |
| Background | (no organisms) | 1.2 |

EXAMPLE 13

Accelerated Solution Hybridization[12]/ of rRNA from *Legionella pneumophilia* with Separation of the Hybrid on Magnetic Amine Microspheres

[12]/ Patent pending on accelerated rate system.

In this experiment, the use of magnetic amine microspheres for the detection of *Legionella pneumophilia* rRNA in sputum was demonstrated with accelerated solution hybridization. The materials were the same as those described in Example 11, except that individual sputa were used instead of pooled sputa. Additionally, 5 ml screw-capped tubes were purchased from Vanguard (Sweden); glass beads (0.2–0.3 man) from Glen Mills, Inc., Maywood, N.J., USA; the ultrasonic cleaner from Branson Equipment Co., Shelton, Conn., USA (Model 1200); and the Corning magnetic separator rack from Advanced Magnetics, Inc. (catalog #M4700).

Individual sputa were liquified as described in Example 5 for pooled sputa. The liquified sputa were then seeded with *Legionella pneumophila* (see Example 10) such that 0.1 ml contained 10⁴ organisms. To 5 ml tubes were added 100 μl glass beads (acid washed), 100 μl lysis buffer (20% SDS, 10 mM EDTA, 10 mM EGTA, 50 mM Tris, pH 8.0) and 0.1 ml seeded sputum or 0.1 ml negative control (1 mg/ml calf thymus DNA in 0.1% SDS), all in triplicate. The samples were then sonicated for 15 minutes at 72° C., 2 ml probe solution (44% DIBSS, 50 mM PB, pH 6.8, 10,000 cpm Legionella specific DNA probe per 2 ml) was added, the mixture was vortexed and then incubated for 1 hour at 72° C. The hybrids were then isolated according to one of the following procedures (all in triplicate): 1. HAP, centrifugation—2 ml of separation solution (5% HAP in 0.26M PB, pH 6.8, 0.02% SDS) was added to each tube, the tubes were inverted 5×, incubated at 72° C. for five minutes, inverted 20×, then centrifuged for 2 minutes at 2000×g. The supernatant was decanted off and discarded, 4.5 ml wash solution (0.14M PB, pH 6.8, 0.02% SDS) was added, each tube was vortexed 20 seconds, and the HAP was pelleted and the supernatant decanted as described above. Each tube was then counted for radioactivity in a Berthold gammacounter. 2. Magnetic amine microspheres, centrifugation—2.75 ml magnetic separation solution (9.5% Triton, 0.15M PB, pH 6.8, 150 l magnetic amine microspheres per 2.75 ml solution) was added to each tube, and the tubes were worked up as in procedure 1 with the following exceptions: wash solution was 18% DIBSS, 5% Triton, 0.1M PB; after addition of wash solution, the tubes were inverted to remix the magnetic amine microspheres. 3. Magnetic amine microspheres, magnetic separation—this procedure is exactly like procedure 2 with the exception that centrifugation is replaced with magnetic separation using the Corning magnetic separator rack. The results are shown in Table 10.

TABLE 10

| | % cpm bound | | |
|---|---|---|---|
| Method | Control | Hybrid | Hybrid:Control |
| 1 | 1.9 | 8.2 | 4.3 |
| 2 | 0.75 | 5.1 | 6.8 |
| 3 | 0.48 | 5.5 | 11.5 |

Method 1 = HAP, centrifugation. Method 2 = magnetic amine microspheres, centrifugation. Method 3 = magnetic amine microspheres, magnetic separation. Control values represent the average of 4 separate determinations, each done in triplicate. Hybrid values represent the average of 30 separate determinations (30 individual sputa) each done in triplicate.

EXAMPLE 14

Use of Magnetic Propylamine Microspheres to Separate rRNA

To show that the method of the invention is not limited to the properties of a single type of magnetic cationic microsphere as a support surface but includes other cations, [³H]-rRNA was removed from defined buffers with magnetic proplyamine microspheres. The materials were the same as those described in Example 1, except that the microspheres were N-3-aminopropyl silane magnetic microspheres (Advanced Magnetics, Inc., special order).

The method used here for removing [³H]-rRNA was exactly the same as that used in Example 1, except that magnetic propylamine microspheres were used in place of magnetic amine microspheres. In 140 mM PB, 93% of the rRNA bound to the microspheres. In a solution of 100 mM PB+1M NaCl, 83% was bound.

EXAMPLE 15

Use of Magnetic Quaternary Ammonium Microspheres to Separate rRNA

Magnetic quaternary ammonium microspheres were synthesized to further study the method of the invention with other polycationic supports. Magnetic amine microspheres (BioMag M4100) were purchased from Advanced Magnetics, Inc. Iodomethane was from Aldrich Chemical Co., Milwaukee, Wis., USA, and 2,6-lutidine was from Sigma Chemical Co., St. Louis, Mo., USA. Other materials were reagent grade.

Magnetic amine microspheres (250 mg, 5.0 ml) were diluted into 10 ml of water. The microspheres were separated magnetically and washed by suspension in 20 ml of 50% (v/v) ethanol/water followed by magnetic separation. This wash process was repeated two times with 20 ml of absolute ethanol. The washed microspheres were then resuspended in 20 ml absolute ethanol. Iodomethane (250 μl, 4 mmoles), and 2,6-lutidine (24.5 μl, 210 μmoles) were added with stirring; stirring was continued overnight at room temperature. The microspheres were then removed magnetically, washed four times with 20 ml water as described above, and resuspended in 5 ml of water for storage at 4° C.

The magnetic quaternary amine microspheres were then used to remove [³H]-rRNA and [³²P] deoxyoligonucleotides from defined buffers to study the ability of the support to distinguish RNA polynucleotides from DNA oligonucleotides in solution. The deoxyoligonucleotide was the 36 mer described in Example 8. All other materials were the same as those described in Example 1.

The binding was determined using the procedure described in Example 1 and the results are shown in Table 11.

TABLE 11

| Reagent System | % [$^3$H]-rRNA Bound | % [$^{32}$P]-DNA Bound |
|---|---|---|
| 0.1M PB, pH 5.7 | 99 | — |
| 0.1M PB, pH 6.8 | 98 | — |
| 0.1M PB, pH 7.8 | 96 | — |
| 0.1M BB$^{13/}$, pH 9.5 | 97 | — |
| 0.1M PB, pH 6.8 | 98 | 62 |
| 0.15M PB, pH 6.8 | 97 | 57 |
| 0.20M PB, pH 6.8 | 97 | 39 |
| 0.30M PB, pH 6.8 | 89 | 6 |

EXAMPLE 16

Use of Magnetic Poly-D-Lysine Functionalized Microspheres to Separate rRNA

In addition to the cationic derivatives described supra in Examples 14 and 15, magnetic microspheres were derivatized with poly-D-lysine.

Materials: Carboxyl terminated magnetic microspheres were purchased from Advanced Magnetics, Inc. (Biomag M4125, containing approximately 250 uequiv. of carboxyl groups per gram). Poly-D-lysine, average degree of polymerization 68 monomer units, was from Sigma Chemical Co., St. Louis, Mo., USA. N,N'dicyclohexyl carbodiimide (DCC) was from Pierce Chemical Co., Rockford, Ill., USA; and N-hydroxysuccinimide (NHS) was from Eastman-Kodak Co., Rochester, N.Y., USA.

Ten milliliters of a 20 mg/ml suspension of carboxyl terminated magnetic microspheres was transferred to a glass teflon lined screw cap test tube. The microspheres were separated magnetically and washed sequentially with 0.1N NaOH (10 ml), 0.1M EDTA (10 ml, pH 7), water (2×10 ml), 50% dioxane/water (10 ml), and dry dioxane (3×10 ml). The microspheres were then resuspended in dry dioxane (10 ml) containing NHS (250 mg). Next, DCC was added (400 mg); the tube was covered with foil to exclude light; and the suspension was mixed by end over end rotation for 15 hours. After magnetic separation, the NHS-modified microspheres were washed sequentially with dioxane (3×10 ml), methanol (3×10 ml), and dry dioxane (3×10 ml), and resuspended in dry dioxane (10 ml). One milliliter of the resulting suspension of NHS-modified microspheres was separated magnetically, washed with dilute aqueous HCl (pH 4.3), and resuspended in a 0.5 ml solution of 0.2M NaHCO3/0.4M NaCl/ 0.05% NaN$_3$ containing poly-D-lysine (7 mg). After 2 hours, an aliquot of a solution of 1M ethanolamine HCl (pH 8.4, 100 µl) was added to cap unreacted NHS ester groups. The microspheres were separated magnetically, washed with water (2×1 ml) and resuspended in water (0.5 ml).

The poly-D-lysine functionalized magnetic microspheres were shown to exhibit binding discrimination between rRNA and a synthetic oligonucleotide (26 mer) as follows:

[$^3$H]-labeled rRNA from E. coli and a [$^{32}$P]-end labeled synthetic oligonucleotide were obtained.

To a screw-cap 1.5 ml polypropylene tube was added poly-D-lysine functionalized microspheres (5 µl), buffer (0.1M sodium phosphate, pH 6.8/0.75M NaCl, 0.5 ml), and an aliquot from either of a solution of [$^3$H]-rRNA or a solution of [$^{32}$P]-oligonucleotide. Resulting suspensions were mixed by vortexing repeatedly over a period of 10 minutes. The supernatants were removed by magnetic separation and transferred to vials containing scintillation fluid (5 ml, Betagel™ cocktail). Radioactivity was then quantified by scintillation counting:

[$^{32}$P]-oligonucleotide bound to microspheres: 0–3%
[$^3$H]-rRNA bound to microspheres: 78–82%

EXAMPLE 17

Use of Magnetic Amine Microspheres in a Chemiluminescent Nonisotopic Assay

To demonstrate the ability of magnetic amine microspheres to be used as a separation support for a non-isotopic assay system, separation of hybrids formed using a synthetic deoxyoligonucleotide probe labeled with a chemiluminescent acridinium ester was studied. In addition to the materials listed in Example 1, a deoxyoligonucleotide probe (33-mer) specific for Chlamydia trachomatis rRNA was synthesized and labeled with a chemiluminescent acridinium ester (AE) as described in U.S. patent application Ser. No. 105,080 entitled "Acridinium Ester Labeling and Purification of Nucleotide Probes" filed Oct. 2, 1987 by Arnold, et al., Chlamydia trachomatis rRNA was used and assay tubes were 12×75 mm polystyrene tubes. All other components were reagent grade.

The AE-labeled probe was hybridized to its target RNA (in this case, Chlamydia trachomatis) according to the following procedure:

Hybridization mixture
200 µl hybridization buffer (0.1M lithium succinate, pH 5.2, 10% lithium dodecyl sulfate, 2 mM EDTA and 2 mM EGTA)
1 µl RNA ($10^{-3}$ µg)
1 µl AE-probe (0.125 pmol)

The control mixture was the same as the hybridization mixture except that it contained water instead of RNA. The mixtures were incubated 30 minutes at 60° C., 2 ml of separation solution containing 0.4M PB, pH 6.0, 5% (v/v) Triton X-100, 8% (wt/v) DIBSS and 2.5 mg of magnetic amine microspheres (BioMag M4100) was added, the mixtures were vortexed and incubated an additional 5 minutes at 60° C. The magnetic amine microspheres were then magnetically pulled to the side of the tube, the supernatant was decanted off, and the magnetic amine microspheres were washed 3 times with 2 mL 0.4M PB, pH 6.0, pre-warmed to 60° C. (add wash buffer, vortex, magnetically separate, decant). The bound probe was then eluted from the magnetic amine microspheres by adding 300 µl of elution buffer containing 0.2M PB, pH 6.0, 50% formamide, vortexing and incubating 5 minutes at 60° C. The magnetic amine microspheres were magnetically pulled to the side of the tube, and the solution was transferred to a new assay tube. The chemiluminescence of each sample was then measured in a Berthold Clinilumat Model LB9502 (Wildbad, West Germany) by automatic injection of 200 µl of 0.25 N HNO$_3$, 0.1% H$_2$O$^2$, followed after a one second delay by 200 µl of 1N NaOH and reading of chemiluminescence for 5 seconds (results given in "relative light units, or rlu).

RESULTS:
Control—160 rlu
$10^{-3}$ µg rRNA—3929 rlu

These results demonstrated that the magnetic amine microspheres can clearly separate hybridized from unhybridized probe in an assay system utilizing a non-isotopic label. Here we see a very low background (less than 0.01% of input rlu), and very distinct signal even at a very low concentration ($10^{-3}$ μg) of target RNA.

EXAMPLE 18

Use of Magnetic Amine Microspheres in a Chemiluminescent Nonisotopic Assay with a Clinical Specimen To demonstrate the ability of magnetic amine microspheres to be used as a separation support for a non-isotopic assay system in the presence of a clinical specimen, the AE-probe described in Example 17 was used to detect a dilution series of target rRNA in clinical media. In addition to the materials listed in Example 17, throat swab material was obtained from volunteers and placed in 3% lithium dodecylsulfate, 30 mM PB (pH 6.8), 1 mM EDTA and EGTA (this will subsequently be referred to simply as "throat swab"). AE-probe was hybridized in throat swab material to decreasing amounts of its target rRNA (in this case *Chlamydia trachomatis*) according to the following procedure:

50 μl throat swab
6 μl 4.8M PB (pH 4.7)
2 μl AE-probe (1 pmole)
2 μl RNA ($3\times10^{-3}$, $3\times10^{-2}$, $3\times10^{-1}$ μg)

The control mixture was the same as the hybridization mixture except that it contained water instead of RNA. The mixtures were incubated 60 minutes at 60° C., and one-third of each was then separated, washed and eluted as described in Example 17.

RESULTS:
Control—4,049 rlu
$10^{-3}$ μg rRNA—9,500 rlu
$10^{-2}$ μg rRNA—61,000 rlu
$10^{-1}$ μg rRNA—657,000 rlu These results demonstrate that the magneticamine microspheres can clearly separate hybridized from unhybridized probe in the presence of clinical specimen in an assay system utilizing a non-isotopic label. The control is higher here than in Example 17, at least in part, due to a larger amount of probe used in this sample.

EXAMPLE 19

Synthesis of Additional Polycationic Supports

The following supports were synthesized to further demonstrate the use of cationic supports in hybrid separations.

(a) Spermine latex microspheres:

Spermine was chosen in this example because it is a polyamine whose cations are spaced to correspond to the polynucleotide's anions. Latex amine microspheres (2.5% solids, 1μ mean diameter, 0.125 mequiv./g) was purchased from Polysciences, Inc., Warrington, Pa., USA. 1,4-butanediol, diglycidyl ether and spermine were from Aldrich Chemical Co., Milwaukee, Wis., USA. A Millititer 96 filtration unit and 0.22μ Durapore® filters were gifts from Millipore Filter Corporation, Bedford, Mass., USA. All other materials were reagent grade.

The microspheres were first activated with 1,4-butanediol diglycidyl ether: 25 mg (1 ml) of latex amine microspheres was filtered onto a 0.22μ Durapore® filter. The microspheres were then resuspended in 150 μl of 0.6N NaOH containing 2 mg/ml NaBH4, and the slurry was transferred to a glass test tube to which 1,4-butanediol diglycidyl ether (150 μl) was added slowly with swirling. The mixture was vortexed briefly every 10 minutes for a period of 1 hour followed by the addition of 1 ml of water. The microspheres were then filtered as described above and washed with water (2 ml).

The activated microspheres were then reacted with spermine. The epoxide modified microspheres from the reaction above were suspended in 1 ml of 0.1M Na2CO3, pH=11.6, and 75 μl of spermine (warmed to 50° C.) was added with mixing. After reacting 12 hours at room temperature, the microspheres were filtered, washed with water (2 ml), and resuspended in water (800 μl).

(b) Synthesis of Tris (2-aminoethyl) Amine Latex Microspheres ("Tris-Latex"):

Tris (2-aminoethyl) amine was purchased from Aldrich Chemical Co., Milwaukee, Wis., USA. This compound was chosen because its cations are spaced roughly the same distance apart as polynucleotide anions.

Tris-(2-aminoethyl) amine (50 μl) was added to activated microspheres according to the procedure described in part (a) of this example, supra.

(c) Synthesis of Tris (2-Aminoethyl) Amine Sepharose 4b ("Tris-Sepharose"):

Tresyl-activated sepharose 4B was purchased from Pharmacia Fine Chemicals AB, Uppsala, Sweden. Freeze-dried tresyl-activated Sepharose 4B (1 g) was washed on a 0.22μ Durapore® (Millipore Corp., Bedford, Mass., USA) filter with 1 mM HCl (200 ml) over a period of 45 minutes. The gel was then transferred to a 15 ml polypropylene screw-cap tube containing 5 ml of 0.1M NaHCO$_3$ (pH 8)/0.5M NaCl, and 200 μl of tris (2-aminoethyl) amine. The reaction was mixed at room temperature by slow end over end rotation for a period of 2 hours. The gel was recovered by filtration and washed with 10 ml of 0.1M NaHCO$_3$ (pH 8)/0.5M NaCl, followed by 50 ml of 0.1M Tris (pH 8). The derivatized gel was then transferred to a 15 ml screw-cap tube and washed further in 10 ml of 0.1M Tris (pH 8) by end over end rotation for 4 hours. The gel was filtered and washed with 10 ml of 0.1M sodium acetate (pH 4)/0.5M NaCl, followed by 10 ml of 0.1M Tris (pH 8)/0.5M NaCl. This wash cycle was repeated two times. The gel was then suspended for storage at 4° C. in 5 ml 0.1M Tris (pH 8)/0.5M NaCl/0.02% sodium azide.

(d) Synthesis of Tris-(2-Aminoethyl) Amine Acrylic Microspheres ("Tris-Acrylic Microspheres"):

Materials: Tosyl-Activated Acrylic Microspheres were purchased from Kirkegaard & Perry Labs, Inc., Gaithersburg, Md., USA (mean particle size 3μ).

One milliliter of activated microspheres (10% suspension) was transferred to a screw-cap 1.5 ml polypropylene tube. The microspheres were separated by centrifugation at 10,000 rpm for 5 minutes in a Tomy-Seiko Microcentrifuge (Model MR-15A, Tokyo, Japan); the supernatant was removed. Next, 0.1M NaHCO3 (0.9 ml) and tris-(2-aminoethyl) amine (0.1 ml) were added, and the microspheres were resuspended by vortexing. The contents of the tube were mixed by end over end rotation for 16 hours. The amine-modified microspheres were removed by centrifugation, washed with water (5×1 ml), and resuspended in 20 mM sodium phosphate buffered saline containing 0.02% NaN$_3$ (1 ml).

(e) Functionalization of a Hydrophilic Polyurethane Based Membrane with Tris-(2-Aminoethyl) Amine and with Poly-D-Lysine ("Tris-Polyurethane Membrane" and "Poly-D-Lysine Polyurethane Membrane"):

HPI Affinity Membrane (hydrophilic polyurethane base) was obtained from Amicon Corp., Danvers, Mass., USA. The approximate pore size and thickness of this membrane were given as 1.2 micron and twelve thousandths of an inch, respectively. 2-flouro-1-methylpyridinium phosphate (FMP) was purchased from Aldrich Chemical Co., Milwaukee, Wis., USA; poly-D-lysine (average 68 monomers per molecule) was from Sigma Chemical Co., St. Louis, Mo., USA.

The available hydroxyl groups on the membrane were activated with FMP by a modification of a procedure reported by T. T. Ngo, *Biotechnology*, 4, 134 [1986]. 1×1 cm squares of the membrane were transferred to a 15 ml flat bottom screw cap vial and washed twice with dry acetonitrile (5 ml). The squares were then suspended in dry acetonitrile (4 ml) containing redistilled triethylamine (80 µl); and a solution of FMP (200 mg) in dry acetonitrile (10 ml) containing triethylamine (100 µl) was added dropwise with swirling. The contents of the vial were then swirled on a rotating platform for one hour, after which the solution was removed and the membrane pieces were washed sequentially with acetonitrile (2×5 ml), acetone (5 ml), 50:50 acetone/aqueous 5 mM HCl (5 ml) and aqueous 5 mM HCl (5 ml). The FMP activated membrane squares were then divided between two glass vials and treated with 5 ml of 0.5M $NaHCO_3$ containing either tris-(2-aminoethyl) amine (100 µl) or poly-D-lysine (50 mg). The contents of each vial were mixed on a rotating platform for 15 hours. Finally, the amine-derivatized membrane pieces were washed sequentially with 1M NaCl (3×5 ml), 0.1M sodium phosphate buffer pH 7 (3×5 ml) and water (3×5 ml), and were then blotted dry on a sheet of 3MM paper (Whatman Ltd., Maidstone, England) and stored dry at room temperature.

EXAMPLE 20

Separation of Nucleic Acids with Spermine Latex Microspheres

Spermine latex microspheres were prepared as described in Example 19. Stock [$^3$H] rRNA was from *E. coli* as described, supra. [–32P] ATP was from New England Nuclear Research Products, Inc., Boston, Mass., USA; and T4 polynucleotide kinase was from Bethesda Research Labs, Inc., Gaithersburg, Md., USA. Betagel™ (liquid scintillation cocktail) was from WestChem, San Diego, Calif.

Probe synthesis and labeling: a deoxynucleotide with the sequence "5'-GGCCGTTACCCCACCTACTAGCTAAT-3'" was produced using an Applied Biosystems, Inc. Model 380A DNA Synthesizer (Foster City, Calif., USA) using standard phosphoramidite chemistry[14]/. (This sequence is complementary to the bases 235–260 of the 23S subunit of the *E. coli* ribosome). This oligomer was labeled on the 5'-end using [–32P] ATP and T4-polynucleotide kinase according to the procedure of Maxam and Gilbert (*Proc. Natl. Acad. Sci. U.S.A.*, 74, 560 [1977]).

[14]/ Probe sequence patent pending.

[$^3$H]-rRNA and [$^{32}$P]-DNA immobilizations: 0.5 ml of test buffer, 20 µl of spermine latex microspheres and 0.5 µl of either [3H]-rRNA (14,000 CPM) or [32P] DNA oligomer (15,000 CPM) were mixed and incubated at 50° C. for five minutes. The microspheres were then pelleted by centrifugation at 13,000 RPM for two minutes in a Tomy Seiko Model MR-15A Microcentrifuge (Tokyo, Japan). The supernatants were removed and added to 15 ml of Betagel™ in 20 ml polypropylene tubes. The amount of [3H] or [32P] in each sample was determined using a Nuclear Chicago scintillation counter.

The results are shown in Table 12. At concentrations between 200 mM and 400 mM PB, the spermine latex microspheres maximally removed target polynucleotides and minimally bound probe oligonucleotides. The preferential selection continued into higher buffer concentrations.

TABLE 12

| Buffer Strength | % [$^3$H]-rRNA Bound to Spermine Latex | % [$^{32}$P]-DNA Oligomer Bound to Spermine Latex |
|---|---|---|
| 10 mM PB | 98.0% | — |
| 50 mM PB | 98.4% | 95.7% |
| 100 mM PB | 97.6% | 92.9% |
| 200 mM PB | 95.2% | 41.2% |
| 400 mM PB | 93.5% | 6.5% |
| 600 mM PB | 57.3% | — |
| 800 mM PB | 78.5% | — |

EXAMPLE 21

Separation of Nucleic Acids with Tris-Latex Microspheres

Tris-latex microspheres were prepared as described in Example 19, supra. Other materials are described in Example 20.

Manipulations were as described supra using Tris-latex microspheres in place of Spermine latex microspheres. Results are shown in Table 13. As with spermine latex, the Tris-latex microspheres showed optimum selection of polynucleotide targets over oligonucleotide probes at 200 mM to 400 mM PB.

TABLE 13

| Buffer Strength | % [$^3$H]-rRNA Bound to Tris-Latex | % [$^{32}$P]-DNA Bound Bound to Tris-Latex |
|---|---|---|
| 10 mM PB | 92.0% | — |
| 50 mM PB | 97.2% | 64.6% |
| 100 mM PB | 97.4% | 69.4% |
| 200 mM PB | 98.5% | 16.5% |
| 400 mM PB | 96.8% | 8.3% |
| 600 mM PB | 70.3% | — |
| 800 mM PB | 79.4% | — |

EXAMPLE 22

Separation of Nucleic Acids with Tris-Sepharose

Tris-sepharose was prepared as described in Example 19. Other materials are described in Example 20. Tris-sepharose (100 µl) was added to 0.5 ml of 0.3M PB and 0.5 µl of either [$^3$H]-rRNA or [$^{32}$P] DNA oligomer. The contents were incubated at 60° for 15 minutes with frequent swirling to suspend the gel. The gel was pelleted by centrifugation at 13,000 RPM for 30 sec. and the supernatant was removed and transferred to a 20 ml polypropylene vial containing 15 ml of Betagel™. The gel was washed two times with 0.5 ml of 0.3M PB; the washings were separated by centrifugation and transferred to polypropylene vials containing Betagel™ as described above. Finally, the gel was suspended in 0.5 ml of 0.3M PB and likewise transferred to a polypropylene vial containing 15 ml of Betagel™. The amount of [$^3$H] or [$^{32}$P] in each sample was determined by scintillation counting as described supra. The results in Table 14 show the preferential binding of RNA polynucleotide over DNA oligonucleotide.

TABLE 14

| Sample | Percent Bound to Gel |
| --- | --- |
| [$^3$H]-rRNA | 75.1% |
| [$^3$H]-rRNA | 80.6% |
| [$^{32}$P]-DNA (26-mer) | 0.54% |
| [$^{32}$P]-DNA (26-mer) | 0.71% |

EXAMPLE 23

Separation of Nucleic Acids with Tris-Acrylic Microspheres

Binding discrimination of the tris-(2-aminoethyl) amine derivatized acrylic microspheres (described in Example 19, supra) for rRNA versus a synthetic oligonucleotide was demonstrated. [$^3$H]-rRNA from *E. coli* and a [$^{32}$P] end-labeled oligonucleotide (26 mer) are described in Example 20. To a 1.5 ml screw cap polypropylene tube were added: tris-(2-aminoethyl) amine modified microsphere suspension (7 µl), sodium phosphate buffer (pH 6.8, 200 ul, ranging from 0.1–0.4M), and either of a solution of [$^3$H] rRNA or a solution of [$^{32}$P]-labeled oligonucleotide (1 µl). The suspension was heated at 50 C for 10 minutes, and then was transferred to a well of a microtiter filtration manifold (0.22µ pore size, Millipore, Inc., Bedford, Mass., USA). Vacuum was applied, and the microspheres were washed on the filter with the same buffer (200 µl). The vacuum was released and the microspheres were then resuspended in 20 mM sodium phosphate buffered saline (200 µl) and transferred to a vial containing scintillation cocktail (10 ml, Betagel™). Radioactivity remaining bound to the microspheres was quantitated by scintillation counting. The data is summarized in Table 15.

TABLE 15

| | PERCENT BOUND | |
| --- | --- | --- |
| Buffer | [$^3$H]-rRNA | [$^{32}$P]-DNA Probe |
| 0.1M PB | 74% | 18% |
| 0.2M PB | 71% | 7% |
| 0.3M PB | 61% | 6% |
| 0.4M PB | 47% | 7% |

EXAMPLE 24

Separation of Nucleic Acids with Poly-D-Lysine Polyurethane Membrane and Tris-Polyurethane Membrane The poly-D-lysine modified membrane pieces described in Example 19, supra, were shown to exhibit similar binding discrimination for rRNA versus a synthetic oligonucleotide (19 mer) as has been already described, supra.

[$^3$H]-rRNA from *E. coli* and a [$^{32}$P] end-labeled oligonucleotide (19 mer) were used. Pieces of amine modified membrane were positioned on top of three sheets of 3MM paper (Whatman, Ltd., Maidstone, England) in a slot blotting device (J. M. Specialty Parts, San Diego, Calif., USA). 1 ul aliquots of either [$^3$H]-rRNA or [$^{32}$P]-labeled oligonucleotide were diluted into 200 µl of either Buffer A (0.1M sodium phosphate (pH 6.8)/0.15M NaCl/0.02% SDS/0.1% Triton X-100) or Buffer B (0.1M sodium phosphate (pH 6.8)/0.45M NaCl/0.02% SDS/0.1% Triton X-100. The resulting solutions were then loaded into appropriate wells of the slot blotter and passed through the pieces of amine modified membrane by capillary action. The membrane pieces were then removed from the slot blotter, washed with the same buffer (either Buffer A or Buffer B, 2×2 ml), and transfered to vials containing 5 ml of scintillation cocktail (Betagel™). Radioactivity bound to the membrane pieces was quantitated by scintillation counting; the results are given in Table 16.

TABLE 16

| | | Percent bound | |
| --- | --- | --- | --- |
| Amine Modifier | Buffer | [$^3$H]-RNA | [$^{32}$P]-DNA Probe |
| Poly-D-lysine | A | 49% | 1% |
| Poly-D-lysine | B | 31% | 0.4% |
| Tris-(2-aminoethyl)-amine | A | 8% | 0.3% |
| Tris-(2-aminoethyl)-amine | B | 8% | 0.2% |

EXAMPLE 25

Use of Tris-Latex Microspheres with a Biotinylated DNA-Probe in a Colorimetric Assay To determine the feasibility of the method of the invention for a colorimetric hybridization assay, tris latex microspheres were used in conjunction with a biotin labeled DNA probe to *Mycoplasma pneumoniae* rRNA:

(a) Synthesis of a biotin labeled DNA oligomer complementary to a region of *Mycoplasma pneumoniae* rRNA:

Materials: Biotinyl-E-Aminocaproic acid N-hydroxysuccinimide ester (Biotin-X-NHS) was purchased from Calbiochem-Behring Corp., San Diego, Calif., USA. 5-Allylamine UTP, terminal deoxynucleotide transferase, and 5× tailing buffer were products of Bethesda Research Laboratories, Gaithersburg, Md., USA. Bio-Gel P-60 (100-100 mesh) was from Bio-Rad Laboratories, Richmond, Calif., USA; and Sephadex G-25 (medium) was from Pharmacia Fine Chemicals, Piscataway, N.J. Other materials used are described in Examples 19 and 20, supra. A deoxyribonucleotide probe 36 nucleotides in length, complementary to a sequence present in the 16S subunit of rRNA from *Mycoplasma pneumoniae*, was used. This oligomer was labeled on the 5'-end with [$^{32}$P] as described in Example 20.

Tailing reaction with allylamine UTP: 9 pmol of [$^{32}$P]-oligomer was reacted with 0.1 mM allylamine UTP and 40 units of terminal deoxynucleotide transferase in 50 µl of 1× tailing buffer at 37° C. for 1 hour. The tailed oligomer was purified on a Bio-Gel P-60 column (0.7×10 cm), eluting with 0.1M PB/2 mM EDTA. The oligomer was then desalted by passing it through a Sephadex G-25 column and eluting with 0.2M triethylammonium bicarbonate (TEAB, pH 8).

Reaction with biotin-X-NHs: The allylamine UTP tailed oligomer, dissolved in 150 µl of 0.1M NaHCO$_3$ (pH 8.8)/ 0.02% SDS, was treated four times with 10 µl of biotin-X-NHS (30 mM stock in DMSO) at 60 minute intervals. The biotinylated oligomer was purified on a column of Sephadex G-25 (0.7×10cm) eluting with 0.1M PB/2 mM EDTA/0.02% SDS.

(b) Immobilization of the biotinylated DNA probe-rRNA Hybrid on "Tris-Latex": A stock solution of rRNA (1 ug/ul) from *Mycoplasma pneumoniae* was used. A suspension of tris-latex was prepared as described in Example 19. Other materials were reagent grade.

Hybridization reaction mixtures were as follows:

Hybrid: 1 μl rRNA (1 μg), 10 μl biotinylated DNA probe (0.1 pmol), 0.4 μl 1% SDS, 2.4 μl 1M PB, and 6.2 μl H$_2$O totaling 20 ul.

Probe Control: 10 μl biotinylated DNA probe (0.1 pmol), 0.4 μl 1% SDS, 2.4 μl 1M PB, and 7.2 μl H$_2$O totaling 20 μl.

The hybridization mixtures were incubated at 60° C. for one hour followed by the addition of 0.5 ml of 0.4M PB/0.02% SDS/1.0% Triton X-100 as well as 10 μl tris-latex (aqueous suspension). The contents were mixed and incubated at 60° C. for 5 minutes. The tris-latex microspheres were pelleted by centrifugation at 13,000 RPM for 2 minutes. The amount of [$^{32}$P] remaining bound to the microspheres was determined by scintillation counting using Cerenkov radiation.

In the hybrid experiment, 61% of the total radioactivity bound to the tris latex, while in the probe control only 5% bound. This reflects a 56% hybridization in the former experiment.

(c) The biotinylated DNA probe-rRNA hybrid was non-isotopically detected on Tris-Latex:

Reagents for the preparation of an avidin-alkaline phosphatase complex were purchased from Vector Laboratories, Burlingame, Calif., USA. Bovine serum albumin (BSA), nitro blue tetrazolium salt (NBT), 5-bromo-4-chloro-3-indolyl phosphate (BCIP) and Tween-20 were products of Sigma Chemical Co., St. Louis, Mo., USA. Other materials are described in Examples 19 and 20.

Two samples of Tris-latex incubated either with biotinylated DNA probe/rRNA hybrid or with biotinylated DNA probe alone (as described in this example, supra) were filtered on a Millititer 96 filtration apparatus employing Durapore® (Millipore Corp., Bedford, Mass., USA) filters. Each sample of filtered solids was resuspended in 200 μl of 3% BSA in 0.1M Tris (pH 7.5)/0.1M NaCl/3 mM MgCl$_2$/0.05% Tween-20, transferred to a 1.5 ml screw-cap polyethylene tube, and incubated at 44° C. for 1 hour. The samples were then filtered as described above, and the filtered solids were resuspended in 200 μl of streptavidin-alkaline phosphatase complex (prepared in phosphate-buffered saline according to the manufacturer's recommendations). After 10 minutes, the samples were filtered and washed two times with 200 μl of 0.1M Tris (pH 7.5)/0.1M NaCl/3 mM MgCl$_2$/0.05% Tween-20, and then once with 200 μl of 0.1M Tris (pH 9.5)/0.1M NaCl/50 mM MgCl$_2$. The filtered solids were then resuspended in 200 μl of 0.1M Tris (pH 9.5)/0.1M NaCl/50 mM MgCl$_2$ containing 0.33 mg/ml (NBT) and 0.17 mg/ml (BCIP). Color development was allowed to proceed for 10 minutes in the dark. The latex particles were then removed by filtration and washed two times with 0.1M NaCl 3 mM MgCl$_2$/0.05% Tween-20.

A blue precipitate, deposited onto the surface of the Tris-latex microspheres, was easily visible for the hybrid sample within about 2 minutes. This was clearly distinguishable from the very faint color development observed for the sample with biotinylated probe alone.

EXAMPLE 26

Use of Tris-Sepharose with a Biotinylated Probe in a Colorimetric Non-Isotopic Assay The hybridization system of Example 25 was used with Tris Sepharose gel instead of tris-latex microspheres.

(a) The hybridized biotinylated probe was immobilized on Tris-Sepharose:

Small columns containing 0.1 ml of Tris-Sepharose (prepared as described in Example 19) were prepared using 1 cc Tuberculin syringes. Hybridization mixtures (prepared as described in Example 25(b)) were dissolved in 0.5 ml of 0.25M PB/0.02% SDS/1.0% Triton X-100, and passed dropwise through the tris-sepharose column over a 5 minute period. The columns were then washed two times with 0.5 ml of the same buffer. The amount of [$^{32}$P] remaining bound to the column was determined by scintillation counting as described in Example 25(b). Tris-sepharose exhibited particularly precise selection of hybrid over probe. Of the hybrid, 81% was bound to Tris Sepharose while 0.0% of the probe control was bound. (The amount of [$^{32}$P] remaining bound in the probe control was not measurable above background.

(b) The biotinylated probe was non-isotopically detected.

The materials were as described in Example 21(c). Small columns of Tris-sepharose were prepared and treated with hybridization reaction mixtures as described in this example, supra. The avidin-alkaline phosphatase complex (0.5 ml, prepared as described in Example 25(c)) was then passed dropwise through the column. After 10 minutes, the remaining avidin-alkaline phosphatase solution was pushed out under slight positive pressure. The gel was washed two times with 0.5 ml of 0.1M Tris (pH 7.5)/0.1M NaCl/3 mM MgCl$_2$ and one time with 0.1M Tris (pH 9.5)/0.1M NaCl/50 mM MgCl$_2$. NBT/BCIP dye reagent (0.5 ml, see Example 25) was then passed slowly through the gel. After 10 minutes, the remaining reagent was pushed out, and the gel was washed two times with 0.5 ml of 0.1M Tris (pH 7.5)/0.1M NaCl/3 mM MgCl$_2$.

Blue color development was visible for the hybrid sample within about 2 minutes. This was easily distinguishable from the sample with probe alone, which was only faintly blue after the 10 minute period of color development. Note: This support did not require the "capping" step with 3% BSA as was needed with the former support (Example 25(c)).

EXAMPLE 27

Use of Tris-Sepharose with an Alkaline Phosphatase Labeled DNA Probe in a Colorimetric Assay The utility of the cationic supports described in Example 19 was further demonstrated in a colorimetric hybridization assay employing an alkaline phosphatase/deoxyoligonucleotide probe conjugate.

Materials: An alkaline-phosphatase labeled synthetic oligonucleotide (26 mer), complementary to rRNA from *E. coli* (hereafter referred to as the "target rRNA"), was prepared by a modification of a procedure described by E. Jablonski et al., *Nucl. Acids Res.*, Vol. 14, p. 6115 (1986). The oligonucleotide sequence was chosen to exhibit minimal cross hybridization to rRNA from *Candida albicans* (referred to hereafter as "non-target rRNA"). Target and non-target rRNA was isolated and purified. NBT and BCIP dyes have been described in Example 25, supra. Other materials were reagent grade.

Hybridization cocktails were prepared in 1.5 ml polypropylene microcentrifuge tubes by adding the oligonucleotide-alkaline phosphatase conjugate (10 μl, 1 pmol), dilutions of either target or non-target rRNA (1 μl, 1–0.0001 μg), 4.8M sodium phosphate buffer (2 μl, pH 6.8), sodium dodecyl sulfate (0.4 µl, 1% solution v/v), and sterile water (13.6 µl): total volumes were 20 µl. These cocktails were hybridized at 50° C. for 30 minutes. Next, 0.3M sodium phosphate (0.5 ml, pH 6.8) and tris-sepharose (about 30 µl bed volume) were added, and the contents were mixed by shaking in a water bath at 50° C. for 10 min. The tubes were then spun briefly in a microcentrifuge and the supernatants were drawn off with a pasteur pipette. The tris-sepharose pellets were then washed sequentially with 0.3M sodium phosphate buffer (3×0.5 ml) followed by 50 mM Tris HCl (pH 8)/0.1M NaCl/1 mM MgCl$_2$/0.1 mM ZnCl2 (2×0.5 ml). The pellets were then resuspended in 300 µl of a solution of 0.1M Tris HCl (pH 9.5)/0.1M NaCl/50 mM MgCl$_2$ containing NBT (0.33 mg/ml) and BCIP (0.25 mg/ml) and incubated at 42 C for four hours. Blue-violet coloration was visible on tris-sepharose pellets resulting from hybridization reactions with as little as 0.001 µg of target rRNA. No coloration was evident on tris-sepharose pellets from the controls with as much as 1.0 µg of non-target rRNA.

EXAMPLE 28

Use of Poly-D-Lysine Polyurethane Membrane with an Alkaline Phosphatase Labeled DNA Probe in a Colorimetric Assay In this experiment, the utility of a cationic membrane as the separation support in a colorimetric assay was demonstrated.

Hybridization reactions were performed as described in Example 27. To these reactions was added 300 µl of dilution buffer (0.1M sodium phosphate (pH 6.8)/0.45M NaCl/0.02% SDS/0.1% Triton X-100). The resulting solutions were passed through pieces of poly-D-lysine membrane by capillary action using a slot blotter apparatus as described in Example 24. The membrane pieces were then removed from the slot blotter and washed with dilution buffer (2×2 ml) and assay buffer (2-amino-2-methylpropanediol HCl (pH 10.2)/0.1M NaCl, 2×4 ml). Then, the membrane pieces were immersed in assay buffer (10 ml) containing NBT (0.33 mg/ml) and BCIP (0.25 mg/ml). After 10 minutes, slots treated with hybridization reactions containing 1 µg or target rRNA gave dark blue-violet coloration, whereas controls containing 1 µg of non-target rRNA gave no coloration.

This colorimetric assay did not require the prehybridization, fixation and blocking steps typically associated with slot-blot assays and therefore represents a significant improvement over the existing art.

EXAMPLE 29

Use of Poly-D-Lysine Polyurethane Membrane in a Chemiluminescent Non-Isotopic Assay The utility of the cationic membrane separation support described in Example 19 was demonstrated in a chemiluminescent nonisotopic hybridization assay employing an acridinium ester (AE) labeled DNA probe.

The methods for generation and detection of chemiluminescent acridinium ester labeled oligonucleotide probes were performed as described in U.S. patent application Ser. No. 105,080 entitled "Acridinium Ester Labeling and Purification of Nucleotide Probes", filed Oct. 2, 1987, incorporated herein by reference. An acridinium ester (AE) labeled oligonucleotide (26 mer) complementary to a sequence in rRNA from E. coli was prepared by incorporating a single acridinium ester per probe molecule. Other materials and reagents are described in Examples 19 and 27, supra.

Hybridization cocktails were prepared in 1.5 ml polypropylene microcentrifuge tubes: AE-labeled probe (2 ul, 1.5× 10$^6$ relative light units, "RLU's"), 1% SDS (v/v, 1 µl), 1M sodium phosphate buffer (pH 4.9, 5 µl), and either of target or non-target rRNA (1 ug/ul, 1 µl), total reaction volume 9 µl. The contents of each tube were incubated at 60 C for 30 minutes. Separation buffer (0.6 ml, 0.1M sodium phosphate pH 6.8/0.15M NaCl/0.02% SDS/0.1% Triton X-100) was added, and the resulting solutions were transferred by capillary action onto pieces of poly-D-lysine modified membrane using a slot blotter apparatus as described supra. The pieces of membrane below each slot were individually washed in separation buffer (3×2 ml), and then were cut in 0.25 cm$^2$ pieces and transferred to 12×75 mm polypropylene tubes (Sarsted, West Germany) containing 200 µl of water. The contents of each tube were quantified for relative chemiluminescence as referenced supra. Specifically, a CliniLumat Model LB 9502 Luminometer was used (Berthold, Wildbad, West Germany) with a two injection cycle: Injection #1—0.25M HNO3/0.1% H$_2$O$_2$ (200 µl), Injection #2—2M potassium phosphate buffer (pH 13.2, 200 µl). Results are given in Table 17.

TABLE 17

| Sample Applied to Membrane | Relative Chemiluminescence |
|---|---|
| Separation Buffer Only | 27,291 |
| Hybridization Reactions, | 21,807 |
| Non-Target rRNA | 51,292 |
|  | 18,961 |
| Hybridization Reactions, | 192,058 |
| Target rRNA | 286,842 |
|  | 242,625 |

EXAMPLE 30

Use of Tris-Sepharose in a Chemiluminescent Non-Isotopic Hybridization Assay

Acridinium ester labeled oligonucleotide probe/rRNA hybridization reactions were run as described in Example 29. Aliquots from these reactions were transferred to clean 1.5 ml polypropylene microfuge tubes and diluted with 0.3M sodium phosphate buffer (pH 6.8, 0.5 ml). Next, tris-sepharose (30 µl bed volume, prepared as described in Example 19) was added, and the contents were mixed by gentle vortexing at room temperature for 10 minutes. After a brief spin in a microcentrifuge, the supernatants were removed and the resulting tris-sepharose pellets were washed with 0.3M sodium phosphate (pH 6.8, 2×0.5 ml) and then suspended in 0.3M sodium phosphate (pH 6.8, 0.5 ml). Aliquots of the resulting suspensions (0.4 ml) were transfered to 12×75 mm polypropylene tubes; and 30% hydrogen peroxide was added (0.5 µl). Chemiluminescence was measured as described in Example 29 except that a single injection of 2N NaOH (200 µl) was used to initiate the chemiluminescent reaction. Results are given in Table 18.

TABLE 18

| Sample Bound to Tris-Sepharose | Relative Chemiluminescence |
|---|---|
| Control (no target) | 637 |
| Target (E. coli rRNA) | 97,071 |
| Non-Target (C. albicans rRNA) | 702 |

Those skilled in the art will appreciate that the methods and compositions described above can be used to purify nucleic acids and to detect target nucleotide sequences in DNA and RNA derived from a wide variety of sources including infectious agents such as bacteria, viruses and fungi; cancer cells; and cells which may yield information about genetic diseases such as sickle cell anemia. Accordingly, the scope of this invention will only be limited by reference to the appended claims.

We claim:

1. A method for purifying a polynucleotide greater than 100 nucleotides in length from an impure biological sample comprising an oligonucleotide 10 to 100 nucleotides in length comprising the steps of:

(a) contacting said biological sample with a solid support comprising a plurality of cations selected from the group consisting of ammonium, immonium and guanidinium ions, wherein said polynucleotide binds to said solid support and said oligonucleotide does not bind to said solid support, wherein said polynucleotide is at least three times greater in length than skid oligonucleotide; and (b) separating said oligonucleotide from said solid support while said polynucleotide is held to said solid support.

2. The method of claim 1 wherein said steps are done in a batch mode.

3. The method of claim 1 wherein said solid support is selected from the group consisting of:

a magnetic amine solid support, a magnetic propylamine solid support, a magnetic quaternary ammonium solid support, a magnetic poly-D-lysine functionalized solid support, a poly-D-lysine functionalized polyurethane solid support, a spermine latex solid support, a Tris (2-amino ethyl) amine latex solid support, a Tris (2-amino ethyl) amine beaded agarose solid support, a Tris (2-aminoethyl)-acrylic support, and a Tris(2-aminoethyl) polyurethane amine solid support.

4. The method of claim 1 further comprising the presence of an ionic detergent which does not prevent said polynucleotide from being bound to said solid support.

5. The method of claim 3 further comprising the presence of an ionic detergent which does not prevent said polynucleotide from being bound to said solid support.

6. The method of claim 1 wherein said solid support is washed after said step (b).

7. The method of claim 1 wherein said solid support is treated to recover said polynucleotide after said step (b).

8. The method of claim 1 further comprising treating said solid support with an elution solution to desorb said polynucleotide and then separating said elution solution from said solid support.

9. The method of claim 8 wherein said elution solution is selected from the group consisting of phosphate solution, pyrophosphate solution, tripolyphosphate solution, phytic acid solution and 50% formamide.

10. The method of claim 8 wherein said polynucleotide is recovered from said elution solution.

11. The method of claim 1 wherein said biological sample is a clinical specimen.

12. The method of claim 11 wherein said clinical specimen is selected from the group consisting of body fluid and tissue.

13. The method of claim 11 wherein said clinical specimen is selected from the group consisting of urine specimen, sputum specimen and swab specimen.

14. The method of claim 1 wherein said solid support comprises particles.

15. The method of claim 14 wherein said particles have a size of about 1 micron.

16. The method of claim 14 wherein said particles are magnetically attracted in a manner sufficient to allow or cause said particles to migrate within a magnetic field allowing separation of said particles from solution by use of a magnet.

17. The method of claim 1 wherein said solid support comprises fibers.

18. The method of claim 1 wherein said solid support is a membrane.

19. The method of claim 1 wherein said solid support is formed from material selected from the group consisting of metal oxide, glass, latex, polyamide, polyester, polyolefin, polysaccharide, polyglycol, and polyaminoacid.

20. An assay for detecting a target sequence present on a polynucleotide in an impure biological sample comprising the steps of:

(a) contacting said biological sample with a labelled oligonucleotide probe able to hybridize to said target sequence to form a hybrid;

(b) contacting said hybrid with a solid support, said solid support comprising a plurality of cations selected from the group consisting of ammonium, immonium and guanidinium ions, wherein said hybrid binds to said solid support and forms a bound phase and unhybridized oligonucleotide probe is not bound to said solid support and forms a free phase, wherein said hybrid is at least three times greater in size than said oligonucleotide probe; and (c) detecting the presence of said target sequence by quantitatively or qualitatively measuring the label in said bound phase or said free phase.

21. The assay of claim 20 wherein said hybrid is at least five times greater in size than said oligonucleotide probe.

22. The assay of claim 20 wherein said solid support is selected from the group consisting of:

a magnetic amine solid support, a magnetic propylamine solid support, a magnetic quaternary ammonium solid support, a magnetic poly-D-lysine functionalized solid support, a poly-D-lysine functionalized polyurethane solid support, a spermine latex solid support, a Tris (2-amino ethyl) amine latex solid support, a Tris (2-amino ethyl) amine beaded agarose solid support, a Tris (2-aminoethyl)-acrylic support, and a Tris(2-aminoethyl) polyurethane amine solid support.

23. The assay of claims 20 further comprising the steps of separating said bound phase from said free phase and then washing said bound phase.

24. The assay of claim 20 further comprising the presence of an ionic detergent which does not prevent said polynucleotide from being bound to said solid support.

25. The assay of claim 22 further comprising the presence of an ionic detergent which does not prevent said polynucleotide from being bound to said solid support.

26. The assay of claim 20 wherein said biological sample is a clinical specimen.

27. The assay of claim 26 wherein said clinical specimen is selected from the group consisting of body fluid and tissue.

28. The assay of claim 26 wherein said clinical specimen is selected from the group consisting of urine specimen, sputum specimen and swab specimen.

29. The assay of claim 20 wherein said solid support comprises particles.

30. The assay of claim 29 wherein said particles are magnetically attracted in a manner sufficient to allow or cause said particles to migrate within a magnetic field allowing separation of said particles from solution by use of a magnet.

31. The assay of claim 20 wherein said solid support is formed from material selected from the group consisting of metal oxide, glass, latex, polyamide, polyester, polyolefin, polysaccharide, polyglycol and polyaminoacid.

32. The assay of claim 20 wherein said oligonucleotide probe is an analogue of DNA or RNA, wherein said analogue is selected from the group consisting of alkylphosphonate and arylphosphonate.

33. The assay of claim 32 wherein said analogue is a methyl phosphonate.

34. An assay for detecting a target sequence present on a polynucleotide in an impure biological sample comprising the steps of:
  (a) contacting said biological sample with an oligonucleotide probe able to hybridize to said target sequence to form a hybrid;
  (b) contacting said hybrid with a solid support, said solid support comprising a plurality of cations selected from the group consisting of ammonium, immonium and guanidinium ions, wherein said hybrid binds to said solid support and unhybridized oligonucleotide probe is not bound to said solid support, wherein said hybrid is at least three times greater in size than said oligonucleotide probe;
  (c) separating said solid support from said unhybridized oligonucleotide probe; and
  (d) detecting the presence of said target sequence by quantitatively or qualitatively measuring said oligonucleotide probe which is bound as said hybrid to said solid support or said probe which is not hybridized.

35. The assay of claim 34 wherein said oligonucleotide bound as said hybrid to said solid support is detected by eluting said hybrid, said labelled oligonucleotide probe or the label from said labelled oligonucleotide probe, using an elution solution and quantitatively or qualitatively measuring said hybrid, said labelled oligonucleotide or said label eluted from said solid support.

36. The assay of claim 35 wherein said elution solution is selected from the group consisting of 50% formamide, phosphate solution, pyrophosphate solution, tripolyphosphate solution and phytic acid solution.

37. The assay of claim 34 wherein said hybrid is at least five times greater in size than said oligonucleotide probe.

38. The assay of claim 34 wherein said solid support is selected from the group consisting of:
  a magnetic amine solid support,
  a magnetic propylamine solid support,
  a magnetic quaternary ammonium solid support,
  a magnetic poly-D-lysine functionalized solid support,
  a poly-D-lysine functionalized polyurethane solid support,
  a spermine latex solid support,
  a Tris (2-amino ethyl) amine latex solid support,
  a Tris (2-amino ethyl) amine beaded agarose solid support,
  a Tris (2-aminoethyl)-acrylic support, and
  a Tris(2-aminoethyl) polyurethane amine solid support.

39. The assay of claim 34 further comprising the presence of an ionic detergent which does not prevent said polynucleotide from being bound to said solid support.

40. The assay of claim 38 further comprising the presence of an ionic detergent which does not prevent said polynucleotide from being bound to said solid support.

41. The assay of claim 34 wherein said biological sample is a clinical specimen.

42. The assay of claim 41 wherein said clinical specimen is selected from the group consisting of body fluid and tissue.

43. The assay of claim 41 wherein said clinical specimen is selected from the group consisting of urine specimen, sputum specimen and swab specimen.

44. The assay of claim 34 wherein said solid support comprises particles which are magnetically attracted in a manner sufficient to allow or cause said particles to migrate within a magnetic field, allowing separation of said particles from solution by use of a magnet.

45. The assay of claim 34 wherein said solid support is formed from material selected from the group consisting of metal oxide, glass, latex, polyamide, polyester, polyolefin, polysaccharide, polyglycol and polyaminoacid.

46. The assay of claim 34 wherein said oligonucleotide probe is an analogue of DNA or RNA, wherein said analogue is selected from the group consisting of alkylphosphonate and arylphosphonate.

47. An assay for detecting a target sequence present on a polynucleotide in an impure biological sample comprising the steps of:
  (a) contacting said biological sample with a solid support, said solid support comprising a plurality of cations selected from the group consisting of ammonium, immonium and guanidinium ions, wherein said polynucleotide binds to said solid support to form a bound polynucleotide;
  (b) providing to said bound polynucleotide a labelled oligonucleotide probe able to hybridize to said target sequence to form a hybrid bound by said solid support, wherein said hybrid is at least three times greater in size than said oligonucleotide probe such that said oligonucleotide probe which is not hybridized is not bound to said solid support;
  (c) separating said solid support from unhybridized oligonucleotide probe; and
  (d) detecting the presence of said target sequence by quantitatively or qualitatively measuring said oligonucleotide probe which is bound as said hybrid to said solid support or said probe which is not hybridized.

48. The assay of claim 47 wherein said oligonucleotide bound as said hybrid to said solid support is detected by eluting said hybrid, said labelled oligonucleotide probe or a label from said labelled oligonucleotide probe, using an elution solution and quantitatively or qualitatively measuring said hybrid, said labelled oligonucleotide or said label eluted from said solid support.

49. The assay of claim 48 wherein said elution solution is selected from the group consisting of 50% formamide, phosphate solution, pyrophosphate solution, tripolyphosphate solution and phytic acid solution.

50. The assay of claim 47 wherein said hybrid is at least five times greater in size than said oligonucleotide probe.

51. The assay of claim 47 wherein said solid support is selected from the group consisting of:
a magnetic amine solid support,
a magnetic propylamine solid support,
a magnetic quaternary ammonium solid support,
a magnetic poly-D-lysine functionalized solid support,
a poly-D-lysine functionalized polyurethane solid support,
a spermine latex solid support,
a Tris (2-amino ethyl) amine latex solid support,
a Tris (2-amino ethyl) amine beaded agarose solid support,
a Tris (2-aminoethyl)-acrylic support, and
a Tris(2-aminoethyl) polyurethane amine solid support.

52. The assay of claim 47 further comprising the presence of an ionic detergent which does not prevent said polynucleotide from being bound to said solid support.

53. The assay of claim 51 further comprising the presence of an ionic detergent which does not prevent said polynucleotide from being bound to said solid support.

54. The assay of claim 47 wherein said biological sample is a clinical specimen.

55. The assay of claim 47 wherein said clinical specimen is selected from the group consisting of body fluid and tissue.

56. The assay of claim 54 wherein said clinical specimen is selected from the group consisting of urine specimen, sputum specimen and swab specimen.

57. The assay of claim 47 wherein said solid support is formed from material selected from the group consisting of: metal oxide, glass, latex, polyamide, polyester, polyolefin, polysaccharide, polyglycol and polyaminoacid.

58. The assay of claim 47 wherein said solid support comprise particles which are magnetically attracted in a manner sufficient to allow or cause said particles to migrate within a magnetic field, allowing separation of said particles from solution by use of a magnet.

59. The assay of claim 47 wherein said oligonucleotide probe is an analogue of DNA or RNA, wherein said analogue is selected from the group consisting of alkylphosphonate and arylphosphonate.

60. A kit for detecting a target sequence which may be present on a polynucleotide in an impure biological sample comprising:
(a) an oligonucleotide probe able to form a hybrid with said target sequence; and
(b) a solid support comprising a plurality of cations selected from the group consisting of ammonium, immonium and guanidinium ions, wherein said hybrid is at least three times greater in size than said oligonucleotide probe such that said hybrid binds to said solid support and said oligonucleotide probe does not bind to said solid support in said impure biological sample.

61. The kit of claim 60 wherein said solid support is selected from the group consisting of:
a magnetic amine solid support,
a magnetic propylamine solid support,
a magnetic quaternary ammonium solid support,
a magnetic poly-D-lysine functionalized solid support,
a poly-D-lysine functionalized polyurethane solid support,
a spermine latex solid support,
a Tris (2-amino ethyl) amine latex solid support,
a Tris (2-amino ethyl) amine beaded agarose solid support,
a Tris (2-aminoethyl)-acrylic support, and
a Tris(2-aminoethyl) polyurethane amine solid support.

62. The kit of claim 60 further comprising an ionic detergent which does not prevent said polynucleotide from being bound to said solid support.

63. The kit of claim 60 further comprising an elution solution able to elute said hybrid which is bound to said solid support.

64. The kit of claim 63 wherein said elution solution is selected from the group consisting of phosphate solution, pyrophosphate solution, tripolyphosphate solution, phytic acid solution and 50% formamide.

65. The kit of claim 60 wherein said oligonucleotide probe is labelled to facilitate detection.

66. The kit of claim 60 wherein said oligonucleotide probe is an analogue of DNA or RNA, wherein said analogue is selected from the group consisting of alkylphosphonate and arylphosphonate.

67. The kit of claim 60 wherein said solid support comprises particles.

68. The kit of claim 67 wherein said particles have a size of about 1 micron.

69. The kit of claim 60 wherein said solid support comprises fibers.

70. The kit of claim 60 wherein said solid support is a membrane.

71. The kit of claim 67 wherein said particles are magnetically attracted in a manner sufficient to allow or cause said particles to migrate within a magnetic field allowing separation of said particles from any solution by use of a magnet.

72. The kit of claim 60 wherein said solid support is formed from material selected from the group consisting of metal oxide, glass, latex, polyamide, polyester, polyolefin, polysaccharide, polyglycol, and polyaminoacid.

73. The method of claim 1, wherein said polynucleotide has a length at least 5 times greater than the length of said oligonucleotide.

* * * * *

UNITED STATES PATENT AND TRADEMARK OFFICE
CERTIFICATE OF CORRECTION

PATENT NO. : 5,599,667
DATED : February 4, 1997
INVENTOR(S) : Lyle J. Arnold, Jr. et al It is certified that error appears in the above-indentified patent and that said Letters Patent is hereby corrected as shown below:

On the title page: Item [54] and Column 1, lines 1 and 2,

<u>Line 1 of the Title</u>: Delete "AND" and insert --FOR--

<u>Line 2 of the Title</u>: Insert --,-- after "PURIFICATION"

Column 1, Line 5: Delete "application" and insert --Lyle J. Arnold, Jr., et al., U.S.--

Column 1, Line 8: Delete "PCT/US88/005500" and insert --PCT/US88/00550--

Column 6, Line 40: Before "the" insert --to--

Column 11, Line 32: Delete "physic" and insert --phytic--

Column 13, Line 46: Insert -- [6/] HOAc adjusted to pH 4 w/5N NaOH. Final HOAc conc = 44%.
[7/] wt: vol diisobutyl sulfosuccinate.--

Column 14, Line 16: Delete " [6/] HOAc adjusted to pH 4 w/5N NaOH. Final HOAc conc = 44%.
[7/] wt: vol diisobutyl sulfosuccinate."

Column 16, Line 20: Insert -- [8/] That is, partially neutralized HOAc.
[9/] HOAc/urea, pH 5, was made by combining 840 ul pH 4 HOAc (see Example 4) with 320 mg urea (final volume = 1ml, [urea] = 5.33 M, 66% partially neutralized HOAc).--

Column 23, Line 16: Insert -- [13/] BB = Sodium Borate Buffer.--

UNITED STATES PATENT AND TRADEMARK OFFICE
CERTIFICATE OF CORRECTION

PATENT NO.   : 5,599,667
DATED        : February 4, 1997
INVENTOR(S)  : Lyle J. Arnold, Jr., et al.

It is certified that error appears in the above-identified patent and that said Letters Patent is hereby corrected as shown below:

Column 35, Line 21: Delete "skid" and insert --said--

Column 36, Line 57: Delete "claims" and insert --claim--

Column 39, Line 25: Delete "47" and insert --54--

Signed and Sealed this

Eighteenth Day of August, 1998

Attest:

BRUCE LEHMAN

Attesting Officer

Commissioner of Patents and Trademarks